US006534088B2

(12) United States Patent
Guivarc'h et al.

(10) Patent No.: US 6,534,088 B2
(45) Date of Patent: Mar. 18, 2003

(54) FIBRATE-STATIN COMBINATIONS WITH REDUCED FED-FASTED EFFECTS

(75) Inventors: Pol-Henri W. Guivarc'h, Quebec (CA); Indu Parikh, Durham, NC (US); Robert A. Snow, West Chester, PA (US)

(73) Assignee: SkyePharma Canada Inc., Quebec (CA)

( * ) Notice: Subject to any disclaimer, the term of this patent is extended or adjusted under 35 U.S.C. 154(b) by 0 days.

(21) Appl. No.: 09/838,583

(22) Filed: Apr. 20, 2001

(65) Prior Publication Data

US 2002/0161032 A1 Oct. 31, 2002

Related U.S. Application Data

(60) Provisional application No. 60/270,157, filed on Feb. 22, 2001.

(51) Int. Cl.[7] .............................. A61K 9/16; A61K 9/26; A61K 47/44; A61K 31/222; A61K 31/351; A61K 31/121; A61K 31/22
(52) U.S. Cl. ........................ 424/470; 424/469; 424/489; 424/439; 424/455; 424/484; 424/502; 424/824; 424/464; 514/543; 514/460; 514/687; 514/721
(58) Field of Search .................................. 424/490, 484, 424/474, 464, 489, 469, 470, 439, 455, 502, 824; 514/543, 460, 687, 721

(56) References Cited

U.S. PATENT DOCUMENTS 6,248,363 B1 * 6/2001 Patel et al. ................. 424/422

FOREIGN PATENT DOCUMENTS

| WO | WO 98/35666 | 8/1998 |
| WO | WO 00/30616 | 6/2000 |
| WO | WO 00/37078 | 6/2000 |

* cited by examiner

Primary Examiner—Edward J. Webman
Assistant Examiner—Helen Nguyen
(74) Attorney, Agent, or Firm—Leydig, Voit & Mayer, Ltd.

(57) ABSTRACT

This invention discloses an orally administered pharmaceutical composition for the treatment of elevated levels of cholesterol and related conditions comprising a statin and fenofibrate in the form of microparticles of solid fenofibrate that are stabilized by phospholipid as a surface active substance, wherein a therapeutically effective amount of the composition provides the statin and a quantity of fenofibrate to a fasted human patient that is greater than 80% of the quantity of fenofibrate provided by the same amount of the composition when administered to the same patient who has been fed a high fat meal.

101 Claims, 2 Drawing Sheets

(A) fenofibrate     (B) micronized fenofibrate     (C) Microfluidized fenofibrate

FIBRATE-STATIN COMBINATIONS WITH REDUCED FED-FASTED EFFECTS

This application claims the benefit of U.S. Provisional Application No. 60/270,157, filed Feb. 22, 2001, the entire content of which is hereby incorporated by reference in this application.

This invention relates to therapeutically effective compositions and methods for treatment of patients with dyslipidemia, hyperlipidemia, hypercholesterolemia and related conditions comprising a combination in one dosage form of a hydroxymethylglutaryl coenzyme A (HMG-CoA) reductase inhibitor or statin and a fibrate formulated together to provide simultaneously a therapeutically effective amount of the hydroxymethylglutaryl coenzyme A reductase inhibitor and a therapeutically effective amount of the fibrate taken into the blood of a patient in need of treatment where the amount of the fibrate taken into the blood is not substantially affected by the presence or absence of food or levels of fat in food taken by the patient proximal to the administration of the dosage form. The compositions of this invention are also useful for the prevention of type III hyperlipoproteinemia in patients prone to that condition.

In particular, this invention relates to an oral dosage form of a pharmaceutical composition comprising a combination or a statin, a carbohydrate bulking agent, and microparticles of fenofibrate that are stabilized by a phospholipid surface active substance, wherein the dosage form provides to a patient in need of treatment by the statin and fenofibrate a therapeutically effective dose of the statin and a therapeutically effective quantity of fenofibrate active species to said patient when fasted that is at least 80% and especially at least 85% of the quantity of fenofibrate active species, particularly the AUC quantity of fenofibrate active species, provided by said amount to said patient when fed a meal containing fat, especially when fed at least 1000 calories 50% of which are from fat.

BACKGROUND

In humans, cholesterol and triglycerides (TG) are part of lipoprotein complexes in the bloodstream, and can be separated via ultracentrifugation into high-density lipoprotein (HDL), intermediate-density lipoprotein (IDL), low-density lipoprotein, (LDL) and very-low-density lipoprotein (VLDL) fractions. Cholesterol and triglycerides are synthesized in the liver, incorporated into VLDL, and released into the plasma. High levels of total cholesterol (total-C), LDL-C, and apolipoprotein B (apo-B, a membrane complex for LDL-C) promote human atherosclerosis, and decreased levels of HDL-C and its transport complex, apolipoprotein A, are associated with the development of atherosclerosis. Cardiovascular morbidity and mortality in humans can vary directly with the level of total-C and LDL-C and inversely with the level of HDL-C.

Orally administered statins are hydroxymethylglutaryl coenzyme A (HMG-CoA) reductase inhibitors that are used in patients to lower low density lipoprotein (LDL) cholesterol. Complimentary to this are orally administered fibrates which are used in patients to decrease lipoproteins rich in triglycerides, to increase high density lipoprotein (HDL), and to decrease atherogenic-dense LDL. Patients who take statins or fibrates are frequently on diets with low and variable fat content.

Uptake of a fibrate such as fenofibrate by a patient is sensitive to a positive food effect, hereinafter referred to simply as a food effect. A positive food effect (or food effect) exits when the amount of an active drug taken into the blood from a given oral dosage form by a fasting patient is less than the amount of the active drug taken into the blood from the same dosage form by the same patient who has eaten a fat-containing meal proximal to the time of administration of the dosage form. A negative food effect exits when the amount of an active drug taken into the blood from a given oral dosage form by a fasting patient is more than the amount of the active drug taken into the blood from the same dosage form by the same patient who has eaten a fat-containing meal proximal to the time of administration of the dosage form. The compositions of this invention generally exhibit a positive food effect.

Patients with severe primary hypercholesterolemia often present with blood levels of low density lipoprotein (LDL) cholesterol greater than 190 mg/dl (4.9 mmol/L) and triglyceride levels up to 350 mg/dl (3.9 mmol/L). The use of diet and single-drug therapy does not always decrease LDL cholesterol and triglycerides adequately enough to reach targeted values in patients with primary severe hypercholesterolemia with or without a concomitant increase in triglycerides. In these patients a combination of complementary fibrate therapy and statin therapy can be desirable.

HMG-CoA reductase (3-hydroxy-3-methylglutaryl-coenzyme A) is the microsomal enzyme that catalyzes the rate limiting reaction in cholesterol biosynthesis (Mevalonate). A statin compound is an HMG-CoA reductase inhibitor that inhibits HMG-CoA reductase, and therefore inhibits or interferes with the synthesis of cholesterol. Inhibition of cholesterol synthesis can lead to a reduction in blood cholesterol levels.

A large number of naturally or synthetically obtained or synthetically modified compounds have been found to inhibit HMG-CoA reductase. These compounds form a category of agents useful for practicing the present invention. Traditionally these agents have been used to treat individuals with hypercholesterolemia. Examples include statins, which are commercially available, such as lovastatin and mevinolin disclosed in U.S Pat. No. 4,231,938, pravastatin and pravastatin sodium disclosed in U.S. Pat. No. 4,346,227, fluvastatin and fluvastatin sodium and XU 62-320 disclosed in EP 0 114 027 and U.S. Pat. No. 4,739,073, atorvastatin disclosed in U.S. Pat. No. 5,273,995, itavastatin also known as NK-104 disclosed in EP304063, mevastatin disclosed in U.S. Pat. No. 3,983,140, rosuvastatin, velostatin and synvinolin and simvastatin disclosed in U.S. Pat. Nos. 4,448,784 and 4,450,171, cerivastatin and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624, RE36,520, and U.S. Pat. No. 4,897,402, the disclosures of which patents are incorporated herein by reference.

Lovastatin, an inactive lactone, is a white, nonhygroscopic crystalline powder isolated from a strain of *Aspergillus terreus* that is insoluble in water and sparingly soluble in ethanol, methanol, and acetonitrile. Lovastatin is hydrolyzed after oral ingestion to the corresponding (beta)-hydroxyacid. This metabolite is an inhibitor of 3-hydroxy-3- methylglutaryl-coenzyme A (HMG-CoA) reductase. When formulated for oral administration as Mevacor, tablets can contain 10 to 40 mg of lovastatin together with pharmaceutically acceptable excipients such as cellulose, lactose, magnesium stearate, starch, and butylated hydroxyanisole as a preservative. When taken separately, lovastatin can treat related hyperlipidemia such as reduce plasma total-C, LDL-C, total-C/HDL-C ratio and LDL-C/HDL-C ratio as well as increase HDL-C, and modestly decrease VLDL-C and plasma triglycerides TG. Mevacor can lower total-C and LDL-C to target levels, and reduce elevated total-C and LDL-C levels in patients with primary hypercholesterolemia (Types IIa and IIb). Single daily doses given in the evening can be more effective than the same dose given in the morning, perhaps because cholesterol is synthesized mainly at night. A recommended starting dose of Mevacor is preferably given with a meal. 20 mg once a day can be given with the evening meal. Storage between 5–30° C. (41–86° F.) is preferred.

Fluvastatin (also known as fluvastatin sodium), a synthetic HMG-CoA reductase inhibitor, is a white to pale yellow, hygroscopic powder soluble in water, ethanol and methanol. When formulated for oral administration as Lescol®, capsules can contain 20 to 40 mg of fluvastatin together with pharmaceutically acceptable excipients such as gelatin, magnesium stearate, microcrystalline cellulose, pregelatinized starch, red iron oxide, sodium lauryl sulfate, talc, titanium dioxide, yellow iron oxide and other ingredients. Fluvastatin sodium reduces Total-C, LDL-C, and apolipoprotein B, and moderately reduces triglycerides (TG) while producing an increase in HDL-C of variable magnitude. Following oral administration, fluvastatin is absorbed rapidly and completely with peak concentrations reached in less than 1 hour. Administration with food reduces the rate but not the extent of absorption. Fluvastatin sodium is indicated as an adjunct to diet in the treatment of elevated total cholesterol (Total-C), LDL-C, TG and Apo B levels in patients with primary hypercholesterolemia and mixed dyslipidemia (Frederickson Type IIa and IIb). It is also indicated to slow the progression of coronary atherosclerosis in patients with coronary heart disease as part of a treatment strategy to lower total and LDL cholesterol to target levels.

Atorvastatin (or Atorvastatin calcium 2:1) is a white to off-white crystalline trihydrate powder that is insoluble in aqueous solutions of pH 4 and below, and is very slightly soluble in distilled water, pH 7.4 phosphate buffer, and acetonitrile, slightly soluble in ethanol, and freely soluble in methanol. When formulated in Lipitor® tablets for oral administration, tablets can contain 10 to 80 mg of atorvastatin as well as pharmaceutically acceptable excipients such as calcium carbonate, USP; candelilla wax, FCC; croscarmellose sodium, NF; hydroxypropyl cellulose, NF; lactose monohydrate, NF; magnesium stearate, NF; microcrystalline cellulose, NF; Opadry White YS-1-7040 (hydroxypropylmethylcellulose, polyethylene glycol, talc, titanium dioxide): polysorbate 80, NF; and simethicone emulsion. Atorvastatin can reduce total-C, LDL-C, and apo B in patients with homozygous and heterozygous familial hypercholesterolemia, nonfamilial forms of hypercholesterolemia, and mixed dyslipidemia. Atorvastatin can also reduce VLDL-C and TG and produces variable increases in HDL-C and apolipoprotein A-1. Atorvastatin can reduce total-C, LDL-C, VLDL-C, apo B, TG, and non-HDL-C, and can increase HDL-C in patients with isolated hypertriglyceridemia. Atorvastatin can reduce intermediate density lipoprotein cholesterol (IDL-C) in patients Keith dysbetalipoproteinemia. Food decreases the rate and extent of drug absorption as assessed by Cmax and AUC, but LDL-C reduction is similar whether atorvastatin is given with or without food. Atorvastatin can be administered as a single dose at any time of the day, with or without food. Atorvastatin can reduce total-C, LDL-C, VLDL-C, apo B, and TG, and can increase HDL-C in patients with hypercholesterolemia and mixed dyslipidemia.

Simvastatin is a white to off-white, nonhygroscopic, crystalline powder that is practically insoluble in water, and freely soluble in chloroform, methanol and ethanol. Simvastatin is derived synthetically from a fermentation product of *Aspergillus terreus*. After oral ingestion, simvastatin, which is an inactive lactone, is hydrolyzed to the corresponding (beta)-hydroxyacid form which is an inhibitor of 3-hydroxy-3-methyl-glutaryl-coenzyme A (HMG-CoA) reductase. When formulated as Zocor for oral administration, tablets can contain 5 mg to 80 mg of simvastatin as well as pharmaceutically acceptable excipients cellulose, hydroxypropyl cellulose, hydroxypropyl methylcellulose, iron oxides, lactose, magnesium stearate, starch, talc, titanium dioxide as well as other ingredients including butylated hydroxyanisole which can be added as a preservative. Simvastatin shows no fed-fasted effect when administered immediately before a low-fat meal. Simvastatin can reduce total-C, LDL-C, total-C/HDL-C ratio, and LDL-C/HDL-C ratio as well as decrease TG and increase HDL-C.

Cerivastatin (or Cerivastatin sodium) is a white to off-white hygroscopic amorphous powder that is soluble in water, methanol, and ethanol, and very slightly soluble in acetone. Cerivastatin sodium is a synthetic, enantiomerically pure competitive inhibitor of the enzyme 3-hydroxy-3-methylglutaryl-coenzyme A (HMG-CoA) reductase that catalyzes the conversion of HMG-CoA to mevalonate in an early and rate-limiting step in the biosynthesis of cholesterol. The inhibition of cholesterol biosynthesis reduces the level of cholesterol in hepatic cells which stimulates the synthesis of LDL receptors and increases the uptake of cellular LDL particles. This can lead to a reduction in plasma cholesterol concentration. When formulated as Baycol®, cerivastatin sodium tablets can contain 0.2 to 0.8 mg of cerivastatin sodium for oral administration and can be taken with or without food. Other tablet ingredients can include pharmaceutically acceptable excipients such as mannitol, magnesium stearate, sodium hydroxide, crospovidone, povidone, iron oxide yellow, methylhydroxypropylcellulose, polyethylene glycol, and titanium dioxide. In patients with hypercholesterolemia, cerivastatin sodium can produce reduced levels of plasma total cholesterol, LDL-C, and apolipoprotein B, VLDL-C and plasma triglycerides and increases plasma HDL-C and apolipoprotein A-1. Cerivastatin systemic exposure (area under the curve, AUC) and $C_{max}$ are not sensitive to a food effect, but once daily doses of 0.2 mg can be more efficacious than twice daily doses of 0.1 mg. Cerivastatin sodium can be effective as an adjunct to diet to reduce elevated Total-C, LDL-C, apo B, and TG and to increase HDL-C levels in patients with primary hypercholesterolemia and mixed dyslipidemia (Fredrickson Types IIa and IIb) when the response to dietary restriction of saturated fat and cholesterol and other non-pharmacological measures alone is inadequate.

Pravastatin (or pravastatin sodium) is a white to off-white, fine or crystalline powder. It is a relatively polar hydrophilic compound with a partition coefficient (octanol/water) of 0.59 at a pH of 7.0. It is soluble in methanol and water (>300 mg/mL), slightly soluble in isopropanol, and practically insoluble in acetone, acetonitrile, chloroform, and ether. When formulated as Pravachol for oral administration, tablets can contain 10 to 40 mg of pravastatin. Inactive ingredients can include pharmaceutically acceptable excipients such as croscarmellose sodium, lactose, magnesium oxide, magnesium stearate, microcrystalline cellulose, and povidone. A 10 mg tablet can also contain Red Ferric Oxide, a 20 mg tablet can also contain Yellow Ferric Oxide, and a 40 mg tablet can also contain Green Lake Blend (mixture of D&C Yellow No. 10-Aluminum Lake and FD&C Blue No. 1-Aluminum Lake).

Itavastatin is an inhibitor of HMG-CoA reductase and can be dosed in tablets containing from about 1 mg to about 20 mg, preferably from about 2 mg to about 10 mg.

Rosuvastatin is an inhibitor of HMG-CoA reductase and can be dosed in tablets containing from about 4 or 5 mg to about 10 or 20 mg, with reported doses of up to about 80 mg per day when formulated as Crestor.

Preferred statins in this invention are those useful for oral administration. Most preferred statins in this invention include lovastatin, pravastatin, simvastatin, atorvastatin, rosuvastatin, fluvastatin, itavastatin and cerivastatin.

While blood levels of active drug or active species from an oral dose of a fibrate such as fenofibrate in a patient are susceptible to a food effect (i.e., variable uptake between fed and fasted states) leading to variation in the amount of active drug species received from a given dose of a fibrate, the efficacy of most statins is not substantially compromised by the presence or absence of food. In a combination dosage form of a statin and a fibrate such as fenofibrate, intake or absence of intake of food can lead to unexpectedly high or low levels of the active fibrate in the presence of a given dosage level of a statin. This lack of control of fibrate level in the blood can potentially lead to undesired side effects such as myopathy and rhabdomyolysis that have sometimes been seen previously with statins alone and with fibrates and statins when administered concurrently to a patient, particularly as a result of concurrent administration of gemfibrozil and lovastatin. Administration of separate dosage forms of a statin and of a fibrate can also pose the potential for variable uptake of either drug, for example when a patient overdoses or underdoses one or the other individual dosage form by taking more or fewer doses of either separate drug than the patient's condition would require for treatment. This can happen when a patient forgets to take one or the other drug dosage form, or when the patient forgets that he or she has taken one or the other drug dosage form and subsequently takes a second or even a third or more dosage form of one or both of the drugs. This can be especially prevalent in an older patient and in a patient with a failing memory.

Thus there is a need for a single therapeutically effective oral dosage form comprising a combination of a hydroxymethylglutaryl coenzyme A (HMG-CoA) reductase inhibitor (or a statin) and a fibrate that provides adequate delivery of both a therapeutically effective amount the HMG-CoA reductase inhibitor (statin) and a therapeutically effective amount of the fibrate active species without substantial variability in the amounts of either of the drugs received in a patient between a fasted and fed states. It is an object of this invention to provide such a dosage form.

In this regard, this invention provides a novel pharmaceutical composition comprising a combination of a hydroxymethylglutaryl coenzyme A reductase inhibitor and a fibrate, particularly fenofibrate, in the form of microparticles of solid fibrate that are stabilized by phospholipid as a surface active substance and that provide reduced in vivo variability in the therapeutically effective amounts of either of the drugs in a patient between a fed and fasted states when administered orally. The present invention further provides novel pharmaceutical compositions comprising a combination of a statin and a fibrate. particularly fenofibrate, in the form of microparticles of solid fibrate that are stabilized by phospholipid as a surface active substance and that provide reduced in vivo variability in the bioavailability of the drug among fed and fasted patients when administered orally.

In particular, the present invention provides a dosage form such as an orally administered dosage form of a pharmaceutical composition comprising a combination of a statin and microparticles of fenofibrate that are stabilized by a phospholipid surface active substance, wherein the dosage form provides to a patient in need of treatment by the statin and fenofibrate a therapeutically effective dose of the statin and a therapeutically effective quantity of fenofibrate active species to said patient when fasted that is at least 80% of the quantity of fenofibrate active species provided by said amount to said patient when fed a meal containing fat.

It has long been known that the bioavailability of many hydrophobic drugs can be improved if the drugs are administered with food, i.e., the drugs exhibit a food effect. A patient is often instructed to take the drug at meal times. Various explanations of the food effect have been advanced including delayed gastric emptying to allow more drug to dissolve before reaching the small intestine thereby producing longer residence times at specific absorption sites in the small intestine; direct interaction and solubilization of drug by food, especially by hydrophobic food components such as fats and lipids; food-related increases in hepatic blood flow to cause a decrease in first-pass metabolism; and increased gastrointestinal secretions that can improve drug solubility.

Dosage forms or quantities of compositions containing a fibrate such as fenofibrate have been marketed and prescribed for the treatment of hypercholesterolemia, hyperlipidemia, hypertriglyceridaemia and related disorders. There have been a number of improvements in dosage forms of fenofibrate in an effort to increase bioavailability of the drug and hence its efficacy. However, there is still a need for a dosage formulation that can substantially reduce or overcome the differential between the bioavailability of the drug in patients who are fasted versus the bioavailability of the drug in patients who are fed.

Fenofibrate or 2-[4-(4-chlorobenzoyl)phenoxy]-2-methyl-propanoic acid 1-methylethyl ester is an example of a poorly water-soluble compound. It is a benzophenone containing a para-chlorophenyl group and a para-isopropyloxycarbonylisopropoxyphenyl group, both of which are substantially hydrophobic groups. Fenofibrate exhibits a melting point reported to be in the range of 79 to 82° C. (Physician's Desk Reference, 1999 Edition, pace 477), which is above that of the symmetrically unsubstituted benzophenone with a reported melting point range of 48 to 51° C. but below that of the symmetrically substituted 4,4'-dichlorobenzophenone with a reported range of 144 to 146° C. (Aldrich Chemical Co. catalog, 1999).

Fenofibrate acts as a potent lipid modulator agent offering unique and significant clinical advantages over existing products in the fibrate class of drugs. Fenofibrate produces substantial reductions in plasma triglyceride levels in hypertriglyceridemic patients and in plasma cholesterol and LDL-cholesterol in hypercholesterolemic and mixed dyslipidemic patients.

Fenofibrate is practically insoluble in water. It is normally poorly and variably absorbed, and has to be taken with food.

Fenofibrate is a prodrug that is absorbed and then hydrolyzed by tissue and plasma esterases to fenofibric acid, its active metabolite. The major metabolite of fenofibrate found in blood or plasma, fenofibric acid, has an elimination half-life of approximately twenty hours. Fenofibric acid is a fenofibrate active species responsible for the pharmacological activity of fenofibrate.

Fenofibrate was first available in a pharmaceutical dosage form (Lipidil®) consisting of a hard gelatin capsule containing fenofibrate and pharmaceutically acceptable excipients such as lactose, pregelatinized starch and magnesium stearate. After oral administration, during a meal, about 60% of the dose of this conventional form is absorbed and found in the blood as fenofibric acid (Weil et al., The metabolism and disposition of 14C-fenofibrate in human volunteers, Drug. Metabol. Dispos. Biol. Fate. Chem., 18 (1990) 115–120).

Historically, in order to improve the intestinal absorption, another pharmaceutical dosage form was introduced (Lipidil Micro®). European Patent Application 330,532 and U.S. Pat. No. 4,895,726 disclose a fenofibrate composition in which the fenofibrate powder is co-micronized with a solid wetting agent. Sodium lauryl sulfate is described as the wetting agent of choice. The co-micronized powder so obtained is mixed with capsule filling pharmaceutically acceptable excipients such as lactose, starch, cross-linked polyvinyl pyrrolidone (PVP), and magnesium stearate. A study comparing Lipidil Micro® formulation to the conventional form (Lipidil®) had showed statistically significant increase in bioavailability with the former but without elimination of food effect. A formulation of fenofibrate that refers to this patent is currently available in the United States under the name Tricor Micronized®.

European Patent Application 724,877 describes fenofibrate powder co-micronized with a wetting agent in association with a vitamin E component (tocopherol and/or its organic acid ester) for treating or preventing disorders associated with lipoprotein oxidation.

U.S. Pat. No. 4,800,079 describes a medicinal composition in the form of granules with controlled release of fenofibrate. Each granule includes an inert core, a layer based on fenofibrate and a protective layer. Fenofibrate is present in the form of crystalline microparticles of dimensions not greater than 30 µm.

U.S. Pat. No. 4,961,890 describes a process for preparing a controlled release formulation containing fenofibrate in an intermediate layer in the form of crystalline microparticles (less than 30 µm in diameter) within a multilayer inert matrix.

European Patent Application 757,911 describes a fenofibrate pharmaceutical dosage form in which fenofibrate is in solution in diethylene glycol monoethyl ether (EMDG) which is a non-ionic surfactant.

European Patent Application 904,781 describes a process for making granules of a solid dispersion of a disintegrant in molten fenofibrate by blending a solid dispersing agent into molten fenofibrate, cooling and solidifying the bulk mixture in a tray, and then milling the solid through a screen to produce granules. Disintegrants include polymers such as starch, croscarmellose sodium, sodium starch glycolate, and crospovidone which are pharmaceutically acceptable excipients. Such disintegrants are slow to swell and dissolve in aqueous media. Furthermore, when crosslinked as in the case of crospovidone, a polymeric disintegrant will not be uniformly dissolved in molten drug but rather at best will form micro-domains in molten fenofibrate. In addition, polymeric materials can exhibit phase separation phenomena when distributed in a substance with which there is not complete compatibility. This was shown, in part, by Sheu, M. T. et al., "Characterization and dissolution of fenofibrate solid dispersion systems", Int. J. Pharm. (1994), 103(2), 137–46 using differential scanning calorimetry measurements that found fenofibrate to be incompatible with poly (vinyl pyrrolidone). Thus, preparation of a bulk mixture in the melt followed by solidification and grinding can lead to non-uniform distributions and compositions in granules. This can adversely effect the bioavailability of the active component.

U.S. Pat. No. 5,700,471 discloses a process for the micronization of compounds having low solubility in water by exposing such compounds briefly to a temperature above their respective melting points, dispersing them with turbulence in an aqueous or organic phase, and subsequently cooling the phase to form a fine particle dispersion. However, it is specified (column 2, lines 1–9) that certain substances and specifically fenofibrate are not amenable to processing entirely without organic solvents because their aqueous dispersions agglomerate and cannot be metered. Thus, in example 2 of U.S. Pat. No. 5,700,471, fenofibrate is not directly dispersed in water but rather is first dissolved in a four-fold excess of a water-miscible organic solvent (isopropanol) which must be removed in a subsequent step. Organic solvents can pose flammability risks, exposure dangers to process operators, potential environmental problems, and added expense related to their storage, ultimate removal from a formulation, and disposal. Thus it is desirable to overcome the use of organic solvents where possible.

U.S. Pat. No. 4,880,634 describes a method of production of an excipient system containing a pharmacologically active substance for peroral administration of lipid nano-pellets in an aqueous, colloidal suspension. The method consists of forming a melt of a mixture of at least one surfactant, a pharmacologically active substance, and at least one lipid, dispersing the molten mixture within an aqueous solution at a temperature above the melting point of the lipid to form lipid nano-pellets, and cooling the suspension below the melting point of the lipid. Animal and plant phospholipids such as lecithin and their hydrogenated forms may be employed in the process although the use of chloroform is taught in examples citing phospholipon 100H. The pharmacologically effective substance can be added to the melted lipid in molten form or dissolved or dispersed in the molten lipid.

U.S. Pat. No. 4,895,726 discloses a gelatin capsule dosage form of fenofibrate containing a co-micronized mixture of particles of fenofibrate and a solid surfactant. The dosage form exhibits improved dissolution rate and bioavailability of fenofibrate over that of micronized fenofibrate alone or that of micronized fenofibrate subsequently mixed with solid surfactant. However, the surfactant must be a solid so it can be micronized, and the micronized surfactant in the form of particles is not uniformly juxtaposed or coated on the surface of the fenofibrate particles.

U.S. Pat. No. 5,545,628 discloses a melted and cooled pharmaceutical composition in a hard gelatin capsule for treating hyperlipidemia and/or hypercholesterolemia. The composition contains fenofibrate, one or more polyglycolyzed glycerides, and optionally other polyalkylene glycol polymers that are added to adjust HLB value, melting point, and stability. The composition provides an increased bioavailability of fenofibrate with respect to previously marketed forms of fenofibrate (i.e., non co-micronized Lypantyl 200™ and co-micronized Lypantyl 200 M™).

U.S. Pat. Nos. 5,645,856 and 6,096,338 disclose a composition and method of improving the in vivo bioavailability of a hydrophobic drug from a pharmaceutical composition comprising the drug dispersed or dissolved in a digestible oil containing a hydrophilic surfactant which substantially inhibits the in vivo lipolysis of the digestible oil, wherein there is added to the composition a lipophilic surfactant capable of reducing the inhibitory effect of the hydrophilic surfactant.

U.S. Pat. Nos. 5,776,495 and 6,027,747 disclose a solid dispersion with enhanced bioavailability of a surface active agent and at least one therapeutic agent in a hydrophilic carrier having enhanced solubility in an aqueous medium. The dispersion is prepared by dissolving the therapeutic agent in a volatile organic solvent containing a very hydrophilic polymer and without strong heat or vacuum evaporating the solvent to dryness to form a co-precipitate of therapeutic agent and hydrophilic polymer.

U.S. Pat. No. 5,827,536 discloses soluble fenofibrate pharmaceutical dosage formulations exhibiting improved bioavailability after oral administration. However, the formulations contain fenofibrate as a solution in a solubilizing agent consisting of diethylene glycol monoethyl ether.

U.S. Pat. No. 6,042,847 discloses a three-phase pharmaceutical form exhibiting constant and controlled release of an amorphous active ingredient stabilized with polymers for a single daily peroral application. The first phase consists of a core containing an amorphous active ingredient. polyvinylpyrrolidone and a cellulose ether as carriers and as inhibitors of its crystallization, and a surfactant that improves the solubility of the active ingredient and promotes the absorption of the amorphous active ingredient from the gastrointestinal tract. The second phase contains a cellulose ether and a mixture of mono-, di- and triglycerides as sustained release agents. The third phase is a poorly soluble or gastro-resistant polymeric film coating U.S. Pat. No. 6,068,854 discloses a constant release tablet consisting of a matrix of gelatin in which is dispersed as an emulsion, dispersion or colloid a lipophilic and/or poorly water-soluble pharmaceutical substance with a particle size below 200 micrometers.

U.S. Pat. No. 6,074,670 discloses an immediate-release fenofibrate composition comprising an inert hydrosoluble carrier covered with a layer containing fenofibrate in a micronized form having a size less than 20 micrometers, a hydrophilic polymer and, optionally, a surfactant. In an example cited, a suspension of micronized fenofibrate and sodium lauryl sulfate is suspended in a solution of sodium lauryl sulfate and polyvinylpyrrolidone, sprayed onto 100 to 400 micrometers size lactose particles suspended in a fluidized air bed granulator, and the granulate is placed in capsules or transformed into tablets by mixing with crosslinked PVP, microcrystalline cellulose, colloidal silica, and sodium stearyl fumarate. The composition showed enhanced bioavailability of fenofibrate. However, increased dissolution rates of a formulation of fenofibrate do not translate directly or linearly to increase uptake of the drug, and show that an in vitro experimental result can not necessarily predict the results of an in vivo experiment.

It is generally accepted that water insoluble or poorly water-soluble drugs can be made more bioavailable when presented in the form of small particles. In many cases, it is known that small particles must be stabilized against particle size growth and agglomeration by the addition of one or more surface active agents at some point in the preparation of the particles, especially in a size reduction process that employs the input of mechanical energy. Because they are biocompatible and well tolerated in vivo, preferred surface active agents or particle stabilizers are phospholipids, and preferred small particles of fenofibrate are stabilized by phospholipid particle stabilizers.

Microparticles of water insoluble or poorly soluble substances are small particles having diameters of from nanometers to micrometers and refer to solid particles of irregular, non-spherical or spherical shapes. When the insoluble and poorly soluble substances are therapeutically and diagnostically useful substances, formulations containing them as microparticles or small particles provide some specific advantages over unformulated non-micronized drug particles. These advantages include improved oral bioavailability of drugs that are poorly absorbed from the GI tract, development of injectable formulations that are currently available only in oral dosage form, preparation of inhaled drugs that otherwise could not be formulated for nasal or aerosol delivery as well as other advantages.

Current technology for delivering insoluble drugs as described in U.S. Pat. Nos. 5,091,188; 5,091,187 and 4,725,442 focuses on (a) either coating small drug particles with surface active substances that are natural or synthetic phospholipids or (b) dissolving the drug in a suitable lipophilic carrier and forming an emulsion stabilized with surface active substances that are natural or semisynthetic phospholipids.

U.S. Pat. No. 5,145,684 discloses methods for preparation and dispersions of particles consisting of crystalline drug substance having a surface modifier or surface active substance adsorbed to maintain an effective average particle size of less than about 400 nm. However, the method requires a milling step that can result in impurities being added to the formulation from fractured milling media.

U.S. Pat. Nos. 5,470,583 and 5,336,507 disclose methods for preparation of nanoparticles using a charged phospholipid as a cloud point modifier.

U.S. Pat. No. 5,302,401 discloses compositions and methods for forming nanoparticles with a surface modifier and a cryoprotectant adsorbed thereon.

International Patent Application WO 99/39700 describes the preparation of submicron nanoparticles from a pharmacologically active principle and a composite material consisting of at least one lipidic substance and at least one amphiphilic substance using high pressure homogenization to form a microemulsion of the composite material at a temperature higher than the melting temperature of at least one of the materials forming the composite and in the presence of one or more aqueous surfactants as surface active substances and then cooling the microemulsion to form a dispersion of solid particles.

U.S. Pat. No. 5,785,976 discloses a heated aqueous emulsification and cooling process for the preparation of solid lipid particles. In that process a solid lipid or bioactive agent or a mixture of solid lipids or bioactive agents is melted and stabilizers, i.e., surface active substances, are added either to the lipid or bioactive agent and to the aqueous phase or to the aqueous phase only. The aqueous phase is heated to the temperature of the melt before mixing and may contain stabilizers, isotonicity agents, buffering substances, cryoprotectants and/or preservatives. The molten lipid compounds and the bioactive agents can be emulsified in the aqueous phase by high-pressure homogenization. The homogenized dispersion is then allowed to cool until solid particles are formed by recrystallization of the dispersed agents. Drugs or other bioactive substances to be incorporated into the particles may be melted together with the lipids or may be dissolved, solubilized or dispersed in the lipid melt before an emulsification by homogenization step.

U.S. Pat. No. 5,922,355 discloses a method for preparing submicron size microparticles by particle size reduction methods in which a solid material is reduced in size over a period of time while continuously below the melting point of the material or by precipitation while the particles are stabilized with phospholipids as surface active substances in combination with other surface modifiers to control growth of particle size and enhance storage stability. The use of one or more surface modifiers in addition to a phospholipid provides volume weighted mean particle size values that are much smaller than what can be achieved using phospholipid alone without the use of an additional surface active substance (surfactant) with the same energy input while providing compositions resistant to particle size growth on storage. The phospholipid and the surfactant are both present at the time of particle size reduction.

WO 00/30616 discloses a rapidly dispersing solid dry dosage form comprised of a water insoluble compound existing as a nanometer or micrometer particulate solid which is surface stabilized by the presence of at least one phospholipid, the particulate solid being dispersed throughout a bulking matrix. When the dosage form is introduced into an aqueous environment, the bulking matrix is substantially completely dissolved within less than 2 minutes thereby releasing the water insoluble particulate solid in an unaggregated and/or unagglomerated state. The matrix is composed of a water insoluble substance or therapeutically useful water insoluble or poorly water-soluble compound, a phospholipid and optionally also at least one non-ionic, anionic, cationic, or amphipathic surfactant, together with a matrix or bulking agent and if needed a release agent. The volume weighted mean particle size of the water insoluble particle is 5 micrometers or less.

While these disclosures provide compositions and methods to enhance the bioavailability of fenofibrate from various dosage forms, none address the need to substantially reduce or eliminate the food effect observed with fenofibrate, i.e., the difference between the amount of the drug taken up in a patient who is fasting versus the otherwise enhanced uptake of the drug in the patient who is fed (food effect).

Besides the fibric acid derivatives such as fenofibrate, clofibrate, gemfibrozil, bezafibrate, ciprofibrate, clinofibrate, simfibrate, theofibrate, pirifibrate, plafibride, and binifibrate, there are a number of other classes of drugs which, when administered to patients, reduce cholesterol and/or lipids. These include bile acid sequesters such as cholestyramine, and meglutol, melinamide, sitosterol, tiadenol, probucol, and nicotinic acid. In addition to these there is a relatively new class of drugs referred to as statins. The latter class of drugs include atorvastin, cerivastatin, epastatin, fluvastatin, itavastatin, lovastatin, mevastatin, pravastatin, rosuvastatin, and simvastatin.

Combination of a statin with a fibrate has been shown to produce beneficial effect in the treatment of hyperlipidemia and hyperlipoproteinemia. However, the fibrates used previously have a limitation related to the presence of a food effect and require patient restrictions and relatively higher dosage amounts of each drug. Surprisingly, the compositions of this invention comprising a fibrate, more specifically fenofibrate, together with a statin are substantiall devoid of food effect, particularly with respect to the uptake of the fibrate.

Raza, et al. in WO 0045817 disclosed safe non-interacting drug combinations of a 3-hydroxy-3-methylglutaryl CoA (HMG-CoA) reductase inhibitor and a drug that is either an inducer, inhibitor, or substrate of cytochrome P 450. Particular combinations are useful in treating hyperlipidemia in humans who are receiving immunosuppressive chemotherapy. A preferred combination is the agent and a fibrate drug, the use of such a combination in treating hyperlipidemia in mammals, and medicaments containing such a combination for use in such treatments, Lipantil™, a brand of fenofibrate used is known to have food effects Pan et al. in J. Clin. Pharmacol. (2000), 40(3), 316–323 reported that concomitant administration of fenofibrate and pravastatin did not affect the pharmacokinetics of either fenofibric acid or pravastatin in healthy adult volunteers who received single doses of 201 mg fenofibrate alone, 201 mg fenofibrate+40 mg pravastatin, and 40 mg pravastatin alone. However, the combination of fenofibrate and pravastatin was administered as separate dosage forms, and uptake of fenofibrate is subject to a food effect.

Farnier, M. and Dejager, S. in Am. J. Cardiol. (2000), 85(1), 53–57 reported that the addition of fluvastatin to micronized fenofibrate results in substantial improvement in atherogenic plasma lipids levels in severe primary hypercholesterolemia and is well tolerated. Patients received micronized fenofibrate 200 mg, fluvastatin 20 mg plus micronized fenofibrate 200 mg, or fluvastatin 40 mg plus micronized fenofibrate 200 mg. However, the fenofibrate and the statin were administered in separate dosage forms, and uptake of micronized fenofibrate demonstrates a food effect.

Kayikcioglu et al. in Am. J. Cardiol. (1999), 83(7), 1135–1137 reported that simvastatin 10 mg administered on alternate days with fenofibrate 250 mg is as effective as a daily dose of simvastatin 10 mg and fenofibrate 250 mg in lowering plasma cholesterol, triglycerides, and LDL cholesterol, and increasing HDL cholesterol levels in patients with mixed hyperlipidemia. The fenofibrate and simvastatin were administered in separate dosage forms and uptake of fenofibrate is subject to a food effect.

EP 0 475 148 A1 discloses that tablets containing pravastatin in combination with tablets of a fibric acid derivative were useful for prevention or treatment of type III hyperlipoproteinemia.

EP 0 455 042 A1 discloses a combination of pravastatin and fenofibrate in a single capsule for the treatment of dyslipidemia. However, the combination is prepared by grinding a tablet of pravastatin and a tablet of fenofibrate to a powder for use in a single capsule, and this form of fenofibrate exhibits a food effect.

Ippen et al in WO 0037078 describe a combination of the 3-hydroxy-3-methylglutaryl-coenzyme A inhibitor, cerivastatin with fenofibrate and to its use in the prophylaxis and treatment of disorders and diseases of lipid metabolism. The tablets containing the two actives are prepared by standard wet granulation. Such forms of fenofibrate exhibit a food effect.

Canadian patent 2,048,395 provides a method for preventing or treating type III hyperlipoproteinemia by administering pravastatin alone or in combination with a fibric acid derivative such as fenofibrate. Tablets containing pravastatin and fenofibrate alone or in combined were prepared by standard dry granulation method using fenofibrate that is subject to food effect.

It is an object of this invention to provide an orally administered pharmaceutical composition of a statin and a fibrate that provides a therapeutically effective amount of the statin and the fibrate that substantially increases the bioavailability of the fibrate and substantially reduces the difference between the amount of the active species of the drug taken up in a patient who is fasting versus the amount of the active species of the drug in the patient who is fed (i.e., substantially reducing the food effect).

It is another object of this invention to provide an orally administered pharmaceutical composition of a statin and fenofibrate that provides a therapeutically effective amount of the statin and fenofibrate that substantially increases the bioavailability of the fenofibrate and substantially reduces the difference between the amount of the active species of the drug taken up in a patient who is fasting versus the amount of the active species of the drug in the patient who is fed (i.e., substantially reducing the food effect known to be associated with administration of fenofibrate).

It is well accepted in practice that an improved bioavailability of a drug allows for an appropriate reduction in daily dosage amount.

It is another object of this invention to provide an orally administered pharmaceutical composition of a water-soluble statin and fenofibrate that provides a therapeutically effective amount of the statin and fenofibrate that substantially increases the bioavailability of the fenofibrate and substantially reduces the difference between the amount of the active species of the drug taken up in a patient who is fasting versus the amount of the active species of the drug in the patient who is fed (i.e., substantially reducing the food effect known to be associated with administration of fenofibrate).

It is another object of this invention to provide an orally administered pharmaceutical composition of a water insoluble or poorly water-soluble statin and fenofibrate that provides a therapeutically effective amount of the statin and fenofibrate that substantially increases the bioavailability of the fenofibrate and substantially reduces the difference between the amount of the active species of the drug taken up in a patient who is fasting versus the amount of the active species of the drug in the patient who is fed (i.e., substantially reducing the food effect known to be associated with administration of fenofibrate).

It is another object of this invention to provide a combined pharmaceutical dosage form of fenofibrate and a statin that can be administered in a capsule, a tablet, a powder that can be dispersed in a beverage, or other convenient dosage form such as oral liquid in a capsule as known in the art.

It is another object of this invention to provide a once-a-day pharmaceutically effective single dosage form of fenofibrate and a statin that can be administered to a patient in need of treatment while substantially reducing the food effect known to be associated with administration of fenofibrate.

It is another object of this invention to provide a method of treatment of hypercholesterolemia and related diseases of dyslipidemia and dyslipoproteinemia comprising the administration of dosage forms of the compositions of this invention to a patient in need of treatment.

BRIEF SUMMARY OF THE INVENTION

The present invention provides a dosage form of a pharmaceutical composition comprising a combination of a statin and microparticles of fenofibrate that are stabilized by a phospholipid surface active substance, wherein the dosage form provides to a patient in need of treatment by the statin and fenofibrate a therapeutically effective dose of the statin and a therapeutically effective quantity of fenofibrate active species to said patient when fasted that is at least 80% of the quantity of fenofibrate active species provided by said amount to said patient when fed a meal containing fat.

The present invention also provides a dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is greater than 80% of the quantity of fenofibrate active species provided by said amount to said patient when fed at least 1000 calories 50% of which are from fat.

The present invention also provides an oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species into the blood of said patient when fasted that is between 85% and 115% of the quantity of fenofibrate active species provided by said amount into the blood of said patient when fed at least 1000 calories 50% of which are from fat.

The present invention also provides an oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is at least 85% of the AUC quantity of fenofibrate active species provided by said amount to said patient when fed at least 1000 calories 50% of which are from fat.

The present invention also provides a dosage form of a pharmaceutical composition comprising a combination of a statin and microparticles of fenofibrate that are stabilized by a phospholipid surface active substance, wherein the microparticles of fenofibrate are prepared by a process comprising the steps of:

(a) mixing at high shear an admixture of fenofibrate and a phospholipid substance in an aqueous carrier in the absence of an organic solvent within a first temperature range at or above the melting point of fenofibrate to form a heated suspension wherein fenofibrate is molten;

(b) homogenizing said heated suspension in a first pressure range and within said first temperature range to form a heated homogenate containing fenofibrate;

(c) cooling said heated homogenate to a second temperature range below the melting temperature of fenofibrate to form a transiently stable cooled homogenate containing fenofibrate;

(d) applying a particle stabilizing energetic process to said cooled homogenate within a second temperature range below the melting temperature of fenofibrate and in a second pressure range to form a cooled dispersion of small particles containing fenofibrate, and (e) drying said cooled dispersion to form dried small particles containing fenofibrate.

In another aspect, this invention also provides a method of treatment of dyslipidemia and dislipoproteinemia and related diseases in a patient comprising the administration to said patient of a dosage form of the aforementioned pharmaceutical compositions comprising a combination of a statin and microparticles of fenofibrate.

In another aspect, this invention provides a pharmaceutically effective composition comprising small particles of fenofibrate stabilized by a phospholipid stabilizing agent which when dried in the presence of a sugar and optionally also in the presence of a carbohydrate-derived alcohol can be formulated as a capsule or tablet dosage form for oral administration to patients in need of treatment by fenofibrate. The dosage form provides dosage levels of active agent (e.g., fenofibrate active species) into the blood of a fasting patient and into the blood of a fed patient where the amount of drug or active ingredient that the patient receives in the fasted state differs by less than 25%, preferably by less than 20%, more preferably by less than 15%, even more preferably by less than 10%, and most preferably by less than 5% from the amount of drug or active ingredient that the patient receives in the fed state.

In a clinical study using capsule dosage forms and monitoring the pharmacokinetic comparison of a single dose of a phospholipid-stabilized fenofibrate formulation of this invention versus a comicronized fenofibrate (Lipanthyl 67M) dose in healthy volunteers under fed and fasted conditions, distinct advantages are seen. For example, under fasted conditions, the formulation of this invention provides a statistically significant increase in relative bioavailability of fenofibrate over that of a comicronized formulation as evidenced by a higher mean maximum concentration ($C_{max}$) of the drug and a higher mean AUC (area under the curve). This difference between the two formulations substantially disappears under fed conditions.

When the bioavailability of a comicronized (Lipanthyl 67M) formulation under fed conditions is compared to that under fasted conditions, the $C_{max}$ significantly increases and the mean AUC's significantly increases in fed state. In addition, the mean terminal half-life appears to be shortened.

In contrast and unexpectedly when the bioavailability of fenofibrate formulations of this invention are compared under fed versus fasted conditions, the relative increase in $C_{max}$ is substantially less than the relative increase seen in the Lipanthyl 67M case in fed state, and the relative increase in mean AUC is substantially less than the relative increase seen in the Lipanthyl 67M case in fed state. The relative bioavailability is approximately substantially close to unity, (within 20%) when comparing fasted versus fed conditions using the formulation of this invention. No significant variation in mean terminal half-life is observed.

The phospholipid-stabilized fenofibrate particle formulation of this invention provides a pharmacokinetic profile in which the effect of ingestion of food on the uptake of the fenofibrate active species is substantially reduced over that observed with the commercially available comicronized formulation.

Statins are subject to substantial first pass metabolism in the liver where they inhibit HMG-CoA reductase to reduce production of cholesterol. Efficacies of statins are not substantially reduced by the presence or absence of food.

Small particles or microparticles of fenofibrate of this invention can be conveniently prepared by a microfluidization process in the form of an aqueous suspension. The microfluidization process is a one- or two-stage size reduction process that can be done in the presence of a liquefied or vesiclar surface active agent (e.g., a phospholid such as Lipoid E80), and optionally in the presence additives and/or pharmaceutically acceptable excipients such as sucrose and/or sorbitol, and preferably in an aqueous buffer such as a sodium phosphate buffer. Preferably, when the microfluidization is done in two stages or processing steps wherein the first stage is run at a first temperature above the melting point of the drug and the second stage is run at a second temperature below the melting point of the drug, we refer to such a process as a hot melt microfluidization process. A desired amount of a statin can be conveniently added during any step of the process, and is preferably added in the second stage of microfluidization. Water is then subsequently removed from the suspension by a lyophilization (i.e., a freeze-drying step) or spray drying to form a substantially dry powder comprising a solid matrix containing fine particles of fenofibrate and a statin. The water can also be removed by other means such as by evaporation.

In one embodiment of this invention comprising a hot melt process, when the statin is soluble in water or other aqueous media such as aqueous buffer solutions and/or aqueous solutions containing one or more pharmaceutically acceptable excipients or bulking agents such as carbohydrates including sugars, it can be convenient to add the statin to the fenofibrate-containing aqueous medium as either a solid that readily dissolves in the aqueous medium or as an aqueous solution of the statin. A water-soluble statin can be added to the fenofibrate-containing suspensions or dispersions before or after the microfluidization steps, and preferably before or after the second microfluidization step.

In another embodiment of this invention, when the statin is insoluble or poorly soluble in water, it can be micronized in the presence of a surface active substance, preferably a phospholipid, and more preferably with a phospholipid used to stabilize the particles containing fenofibrate, and then mixed with the suspension of fenofibrate before or after any microfluidization steps, and preferably before or after a microfluidization step done below the melting point of fenofibrate.

Optionally, in another embodiment of this invention, the statin and the fenofibrate can be co-suspended and co-micronized in the presence of a phospholipid stabilizing substance to form microparticles comprising the statin and fenofibrate.

In one aspect, small particles of fenofibrate of this invention stabilized by phospholipid can be prepared as a suspension by a process comprising the steps of (a) mixing at high shear an admixture of a fibrate drug and one or more than one surface active substance in an aqueous carrier in the absence of an organic solvent within a first temperature range at or above the melting point of the poorly water-soluble drug to form a heated suspension containing the drug, then (b) homogenizing said heated suspension in a first pressure range and within said first temperature range to form a heated homogenate containing the drug, then (c) cooling said heated homogenate to a second temperature range below the melting temperature of the poorly water-soluble drug to form a transiently stable cooled homogenate containing the drug, then (d) applying a particle stabilizing energetic process to said cooled homogenate within a second temperature range below the melting point of the drug and in a second pressure range to form a cooled dispersion of stabilized small particles of the drug, and then (e) optionally drying the cooled dispersion to form dried matrix of small particles containing the fibrate wherein a statin can be added at any of the previous steps, preferably after the first homogenization step.

In a typical procedure, a premix of fenofibrate, phospholipid Lipoid E80 (dispensed frozen but liquefied or vesiclized at processing temperatures), and optionally sorbitol and sucrose in 10 millimolar aqueous phosphate buffer at pH 8 is microfluidized above the melting temperature of fenofibrate for about 3 to 10 volume passes, cooled, and further microfluidized after addition of a statin for another 10 volume passes to form a suspension of microparticles stabilized by phospholipid.

Particularly important to this aspect of the preparation of the composition of this invention is the use of two homogenization steps separated by a cooling step. The first homogenization step is done on a heated suspension having the poorly water-soluble drug in a molten phase in the presence of one or more than one surface active substance and optionally in the presence of a statin to provide a heated homogenate containing the drug. The heated homogenate is usually in the form of a microemulsion comprising small molten particles or droplets of drug stabilized by one or more than one surface active substance such as a phospholipid substance. The heated homogenate containing the drug is then cooled to provide a transiently stable cooled homogenate containing the drug. The transiently stable cooled homogenate comprises small particles of drug in which the drug is in a solid phase that may be amorphous, crystalline, or a combination of both. The small particles of the cooled homogenate are stabilized by the surface active substance or substances but the particles are transiently stable with respect to particle size growth and eventual precipitation of solid drug from the aqueous carrier unless further processed by an stabilizing energetic step.

The second homogenization step of this aspect of the invention is done on the cooled homogenate after a cooling step to produce a cooled dispersion of small particles containing the drug and having greater stability to particle growth and precipitation than the cooled homogenate. The second homogenization step is a stabilizing energetic process. It provides small particles that are more stable than the transiently stable particles of the cooled homogenate prepared in the first homogenization step and prevents relatively large crystals and/or agglomerates of the poorly water-soluble drug from forming. The second homogenization step facilitates the formation of stabilized small particles of the poorly water-soluble drug. It also provides overall rapid formation of desired small particles containing the poorly water-soluble drug. Optionally, the small particles can be isolated by a drying process, for example by lyophilization or by spray drying. Thus, the process can provide dried small particles containing poorly water-soluble drug. In the absence of the second homogenization step, very large amounts of the poorly water-soluble drug can precipitate from the transiently stable aqueous cooled homogenate or very large amounts of the poorly water-soluble drug can form a sediment by precipitation from the aqueous carrier.

In one aspect of this invention, we have unexpectedly found that small particles containing the poorly water-soluble drug fenofibrate can be prepared by a process comprising the steps of (a) mixing at high shear an admixture of fenofibrate and a phospholipid substance in an aqueous carrier in the absence of an organic solvent within a first temperature range at or above the melting point of fenofibrate to form a heated suspension wherein fenofibrate is molten;

(b) homogenizing said heated suspension in a first pressure range and within said first temperature range to form a heated homogenate containing fenofibrate;

(c) cooling said heated homogenate to a second temperature range below the melting temperature of fenofibrate to form a transiently stable cooled homogenate containing fenofibrate;

(d) applying a particle stabilizing energetic process to said cooled homogenate within a second temperature range below the melting temperature of fenofibrate and in a second pressure range to form a cooled dispersion of small particles containing fenofibrate, and (e) doing said cooled dispersion to form dried small particles containing fenofibrate.

In this process, a statin can be added to the admixture, to the heated suspension, to the heated homogenate, to the cooled homogenate, to the cooled dispersion, and optionally to the dried small particles such as in a blending step. At which step in the process the statin can be added to provide the best formulation result in terms of particle size, bioavailability or any other desired property of the formulation can be determined by simple experimentation and process optimization by varying concentrations of the ingredients, temperature, processing time, and the like. Addition of the statin at some time after the cooling of the heated homogenate is currently preferred.

Particularly important to this aspect of the invention is the use of two homogenization steps separated by a cooling step and the use of a phospholipid as a surface active substance. The first homogenization step is done on a heated suspension in the presence of a phospholipid as a surface active substance, in the absence of an organic solvent, and wherein fenofibrate is molten to provide a homogenized microemulsion containing fenofibrate. The second homogenization step is done on a transiently stable cooled homogenate in the presence of the phospholipid and wherein the fenofibrate is a solid to provide a homogenized dispersion of small particles containing fenofibrate. In the absence of the second homogenization step, relatively large crystals of fenofibrate otherwise readily form from the transiently stable cooled homogenate. In the absence of a heated first homogenization step on the molten drug, homogenization of solid fenofibrate to provide a suspension of small particles of fenofibrate takes a prolonged or much longer time in the same homogenization apparatus under substantially the same homogenization conditions of pressure and temperature relative to the time taken in the second homogenization step of this invention, and the properties of the dispersions produced by both routes are not identical.

In a preferred aspect of this invention, a stable combination formulation containing fenofibrate and a statin can be prepared if a desired amount of a statin is added to the cooled homogenate just prior to the energetic process of second homogenization in the above described procedure. The resulting dispersion can be dried such as by freeze-drying or spray drying or other suitable drying method, optionally in the presence of one or more sugars, for example sucrose and/or sorbitol, to provide a matrix of the two drugs in the dried sugar. The fenofibrate comprises dried small particles stabilized by the surface active substance. The sugar can be amorphous or crystalline.

It is an advantage of this invention that small particles containing a poorly water-soluble fibrate drug stabilized with one or more than one surface active substances can be prepared in combination with a statin as a dispersion in an aqueous carrier or as dried small particles.

It is another advantage of this invention that a combination of small particles containing a poorly water-soluble fibrate drug and a statin can be prepared in the absence of an organic solvent.

It is another advantage of this invention that a combination of small particles containing a poorly water-soluble fibrate drug stabilized by a phospholipid surface active substance and a statin can be prepared in the absence of an organic solvent.

It is another advantage of this invention that a dosage form comprising a combination of small particles containing a poorly water-soluble fibrate drug and a statin can be prepared using pharmaceutically acceptable excipients such as phospholipids, sugars and polyols.

It is a further advantage of this invention that a suspension of a combination of small particles containing a poorly water-soluble fibrate drug and a statin can be prepared which suspension is relatively stable to mechanical agitation and to growth of larger crystals of drug over a period of time.

It is another advantage of this invention that a matrix of small particles containing fenofibrate and a statin can be prepared without the use of an organic solvent.

It is a further advantage of this invention that a suspension of small particles containing fenofibrate and a statin can be prepared which suspension is relatively stable to mechanical agitation and to growth of larger crystals of drug over a period of time.

It is a further advantage of this invention that a composition of a combined pharmaceutical dosage form of particles of fenofibrate stabilized by a phospholipid surface active agent and a statin is provided that substantially reduces the difference between the amount of fenofibrate taken up in a patient who is fasting versus the amount of fenofibrate taken up in the same patient who is fed.

It is yet another advantage of this invention that a combination pharmaceutical dosage form of fenofibrate and a statin is provided that can be administered orally such as in a capsule, in a tablet, in a powdered form dispersible in a beverage, or suspended or dissolved in a liquid oil form.

It is still another advantage of this invention that a once-a-day pharmaceutically effective combination dosage form of fenofibrate and a statin is provided that can be administered orally to a patient in need of treatment by the drugs without regard to the amount of food a patient has ingested prior to or following administration of the dosage form.

These and other advantages will be readily apparent from the description of the invention.

DETAILED DESCRIPTION OF THE INVENTION

Figure 1:
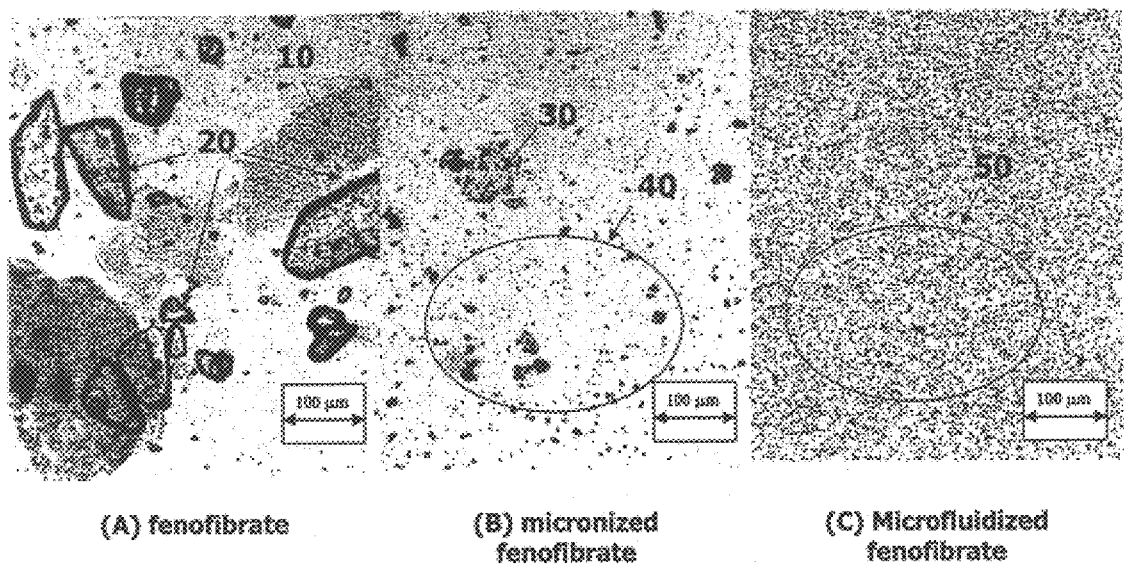
FIG. 1 is an optical microscopic comparison of microfluidized fenofibrate with micronized fenofibrate and fenofibrate compositions prepared in the presence of starch.

The present invention provides an orally administered combination pharmaceutical composition comprising microparticles of solid fenofibrate that are stabilized by a phosphiolipid surface active substance and a statin, wherein said microparticles are preferably prepared in the presence of said phospholipid surface active substance, and wherein a therapeutically effective amount of said composition provides a quantity of fenofibrate to a fasted human patient in need of treatment by fenofibrate that is greater than 80% of the quantity of fenofibrate provided by said amount to said patient when fed a high fat meal comprising at least 1000 calories 50% of which are from fat.

The present invention also provides a dosage form of a pharmaceutical composition comprising a combination of a statin and microparticles of fenofibrate that are stabilized by a phospholipid surface active substance, wherein the dosage form provides to a patient in need of treatment by the statin and fenofibrate a therapeutically effective dose of the statin and a therapeutically effective quantity of fenofibrate active species to said patient when fasted that is at least 80% of the quantity of fenofibrate active species provided by said amount to said patient when fed a meal containing fat. The microparticles are preferably prepared in the presence of said phospholipid surface active substance.

The present invention also provides a dosage form of a pharmaceutical composition comprising a combination of a statin and microparticles of fenofibrate that are stabilized be a phosphiolipid surface active substance, wherein the dosage form provides to a human patient in need of treatment by the statin and fenofibrate a therapeutically effective dose of the statin and a therapeutically effective quantity of fenofibrate active species to said patient when fasted that is greater than 80% of the quantity of fenofibrate active species provided by said amount to said patient when fed at least 1000 calories 50% of which are from fat. The microparticles are preferably prepared in the presence of said phospholipid surface active substance.

The present invention also provides an oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species into the blood of said patient when fasted that is between 85% and 115% of the quantity of fenofibrate active species provided by said amount into, the blood of said patient when fed at least 1000 calories 50% of which are from fat. The microparticles are preferably prepared in the presence of said phospholipid surface active substance.

The present invention also provides an oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is at least 85% of the AUC quantity of fenofibrate active species provided by said amount to said patient when fed at least 1000 calories 50% of which are from fat. The microparticles are preferably prepared in the presence of said phospholipid surface active substance.

The present invention also provides a dosage form of a pharmaceutical composition comprising a combination of a statin and microparticles of fenofibrate that are stabilized by a phospholipid surface active substance, wherein the microparticles of fenofibrate are prepared by a process comprising the steps of:

(a) mixing at high shear an admixture of fenofibrate and a phospholipid substance in an aqueous carrier in the absence of an organic solvent within a first temperature range at or above the melting point of fenofibrate to form a heated suspension wherein fenofibrate is molten;

(b) homogenizing said heated suspension in a first pressure range and within said first temperature range to form a heated homogenate containing fenofibrate;

(c) cooling said heated homogenate to a second temperature range below the melting temperature of fenofibrate to form a transiently stable cooled homogenate containing fenofibrate;

(d) applying a particle stabilizing energetic process to said cooled homogenate within a second temperature range below the melting temperature of fenofibrate and in a second pressure range to form a cooled dispersion of small particles containing fenofibrate, and (e) drying said cooled dispersion to form dried small particles containing fenofibrate.

In another aspect, this invention also provides a method of treatment of dyslipidemia and dyslipoproteinemia and related diseases in a patient comprising the administration to said patient of a dosage form of the aforementioned pharmaceutical compositions comprising a combination of a statin and microparticles of fenofibrate.

This invention also describes an orally administered combination pharmaceutical composition comprising microparticles of solid fenofibrate that are stabilized by a phospholipid surface active substance and a statin, wherein said microparticles are prepared in the presence of said phospholipid surface active substance and one or more excipients, and wherein a therapeutically effective amount of said composition provides a quantity of fenofibrate to a fasted human patient in need of treatment by fenofibrate that is greater than 80% of the quantity of fenofibrate provided by said amount to said patient when fed a high fat meal comprising at least 1000 calories 50% of which are from fat.

As used herein, a fasted patient is defined as a patient who has not eaten any food, i.e., who has fasted for at least 10 hours before the administration of a dosage form of this invention comprising a combination of a statin and microparticles of fenofibrate stabilized by a phospholipid surface active substance and who does not eat any food and continues to fast for at least 4 hours after the administration of the dosage form. The dosage form is preferably administered with 180 ml of water during the fasting period, and water can be allowed ad libitum after 2 hours.

As used herein, a fed patient is defined as a patient who has fasted for at least 10 hours overnight and then has consumed an entire test meal within 30 minutes of first ingestion. The dosage form of this invention is administered with 180 ml of water within 5 minutes after completion of the meal. No food is then allowed for at least 4 hours post-dose. Water can be allowed ad libitum after 2 hours. A high fat test meal provides approximately 1000 calories to the patient of which approximately 50% of the caloric content is derived from fat content of the meal. A representative high fat high calorie test meal comprises 2 eggs fried in butter, 2 strips of bacon, 2 slices of toast with butter, 4 ounces of hash brown potatoes, and 8 ounces of whole milk to provide 150 protein calories, 250 carbohydrate calories, and 500 to 600 fat calories. High fat meals can be used in clinical bioequivalence and bioavailability studies of fenofibrate. High fat meals can promote increased absorption and uptake of fenofibrate.

The compositions and methods of this invention will find utility in treatment of patients suffering from hypercholesterolemia and related lipid disorders described herein. It should be recognized that the definitions of fasted and fed states are primarily for the purposes of clinical comparison with respect to this invention to other dosage forms known in the art. Patients will benefit from the compositions and methods of this invention if they are in the fasted state as defined above, in the fed state as defined above, and also in other fed states where the food consumed contains more or less that 1000 calories and/or more or less than 50% of caloric content derived from fat. Patients who will benefit from the compositions and methods of this invention will often be on a fat restricted diet, a calorie restricted diet, or both, and will naturally consume variable amounts of food from numerous sources at numerous different times of the day, from day to day. The definitions of fasted and fed above are not meant to limit the utility of this invention or to exclude patients in need of treatment by the compositions and methods of this invention.

In a clinical setting, the absence or substantial elimination of a food effect for fenofibrate can be concluded when the 90% confidence intervals for the ratio of the geometric means based on log-transformed data in clinical studies of fed and fasted treatments fall within 80% to 125% for AUC (area under the concentration time curve) and 70% to 143% for $C_{max}$ (peak concentration). The presence of a food effect can be concluded when the 90% confidence intervals for the ratio of the geometric means based on log-transformed data in clinical studies of fed and fasted treatments fall outside 80% to 125% for AUC and outside 70% to 143% for $C_{max}$.

As used herein, "small particle" refers to a particle or a distribution of particles having a diameter or an average diameter, respectively, of from nanometers to micrometers, preferably below 10 micrometers. Small particles are microparticles, as used herein, and also refer to solid particles of irregular, non-spherical or spherical shapes. Preferably the microparticles of this invention have a volume weighted mean particle size smaller than 10 micrometers, more preferably smaller than 5 micrometers, even more preferably smaller then 4 micrometers, even more preferably smaller than 3 micrometers, yet even more preferably smaller than 2 micrometers, yet even more preferably smaller than 1 micrometers, and in some aspects of this invention smaller than 0.5 micrometers.

By "dried" we mean having a water or moisture content greater than zero per cent and below 5% by weight, preferably below 4% by weight, more preferably below 3% by weight, and even more preferably below 2% by weight, and most preferably below 1% by weight. In preferred embodiments. the amount of water is between 0.1% and 3%, more preferably between 0.1% and 2%, and most preferably between 0.1% and 1% by weight. By "anhydrous" we mean have zero water content.

By "transiently stable" we mean that the small particles of the cooled homogenate remain as small particles in a dispersion of the aqueous carrier at substantially the size finally produced in the first homogenization step but for a relatively short period of time and not indefinitely. The period of time that a cooled homogenate remains transiently stable can vary from up to about one second to up to about 48 hours, and preferably from up to about 15 minutes to up to about 24 hours, and most preferably from up to about 6 hours to up to about 24 hours although the period of time can vary with many factors. Unless subsequently treated by a stabilizing energetic step, the transiently stable material can change. For example, as commonly seen in recrystallization of a crystalline substance from an organic solvent, the growth and precipitation of crystals can be induced or enhanced by the presence of seed crystals, by stirring of a cooled supersaturated solution of drug, and by scratching the internal surface of a vessel containing supersaturated dissolved drug below the level of the liquid thereby creating nucleation sites for crystallization. Such factors can affect the time of transient stability in the cooled homogenate of this invention, and such crystal growth is not desirable in the present invention. The transiently stable particles of the cooled homogenate can grow slightly in size (i.e., in average diameter) over the relatively short period of time by as much as 1000% of their original size or more from that size produced in the heated homogenization step, but preferably will remain at the size at which they were produced in the first homogenization step up to a size about 100% larger in diameter, and more preferably up to a size about 50% larger in diameter. After the relatively short period of time, the particles will undesirably continue to become larger such as by Ostwald ripening and crystallization. After the relatively short period of time, drug may also undesirably crystallize in the form of large particles from the suspension. The particles of the heated homogenate may also undesirably and irreversibly agglomerate after the relatively short period of time. Additionally, after the relatively short period of time, the components of the formulation may undesirably phase separate from the aqueous carrier and precipitate and undesirably separate into components that contain largely drug and largely surface active substance unless a stabilizing energetic process is applied to the cooed homogenate.

Examples of some suitable surface active substances that are useful in the hot melt microfluidization process described herein include: (a) natural surfactants such as casein, gelatin, tragacanth, waxes, enteric resins, paraffin, acacia, gelatin, cholesterol esters, phospholipids, and triglycerides, (b) non ionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcelulose, noncrystalline cellulose, polyvinyl alcohol, polyvinylpyrrolidone, and synthetic phospholipids, natural gums (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxylmethylcellulose, and calcium carboxymethylcellulose, (d) cationic surfactants such as quaternary ammonium compounds, benzalkonium chloride, cetyltrimethylammonium bromide, chitosans and lauryldimethylbenzylammonium chloride, (e) colloidal clays such as bentonite and veegum. A detailed description of these surfactants may be found in Remington's Pharmaceutical Sciences, and Theory and Practice of Industrial Pharmacy, Lachman et al, 1986.

More specifically, examples of suitable surface active substances include one or combination of the following: poloxamers, such as Pluronic™ F68, F108 and F127, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylene-diamine available from BASF. Triton™ X-200, which is an alkyl aryl polyether sulfonate, available from Rohm and Haas. Tween 20, 40, 60 and 80, which are polyoxyethylene sorbitan fatty acid esters, available from ICI Specialty Chemicals, Carbowax™ 3550 and 934, which are polyethylene glycols available from Union Carbide, hydroxypropylmethylcellulose, dimyristoyl phosphatidylglycerol sodium salt, sodium dodecylsulfate, sodium deoxycholate, and cetyltrimethylammonium bromide.

Preferred surface active substances are phospholipid surface active substances. By phospholipid surface active substances or phospholipid surface active agents is meant a single phospholipid or a mixture of two or more phospholipids, for example a mixture of two or a mixture of three or a mixture of four or a mixture of five or a mixture of from six to about ten phospholipids. Suitable phospholipids include saturated phospholipids; unsaturated phospholipids; naturally derived phospholipids; synthetic phospholipids and semisynthetic phospholipids; animal and plant phospholipids; egg phospholipids; soya bean phopholipids; corn phospholipids; wheat germ, flax, cotton, and sunflower seed phospholipids; milk fat phospholipids; purified phospholipids from these and other natural sources; glycerophospholipids; sphingophospholipids; phosphatides; phospholipids containing fatty acid esters including palmitate, stearate, oleate, linoleate, and arachidonate which esters can be mixtures and mixtures of isomers in the phospholipids; phospholipids composed of fatty acids containing one or more than one double bonds such as diobloyl phosphatidylcholine and egg phosphatidylcholine that are not stable as powders but are hygroscopic and can absorb moisture and become gummy; phospholipids composed of saturated fatty acids that are stable as powders and are relatively less amenable to absorption of moisture; phosphatidylserines; phosphatidylcholines; phosphatidylethanolamines; phosphatidylinositols; phosphatidylglycerols such as dimyristoyl phosphatidylglycerol. L-alpha-dimyristoyl phosphatidylglycerol also known as 1,2-dimyristoyl-sn-glycero-3-phospho(rac-1-glycerol) and also known as DMPG; phosphatidic acid; hydrogenated natural phospholipids; and commercially available saturated and unsaturated phospholipids such as those available from Avanti Polar Lipids, Inc. of Alabaster, Ala., USA. In the absence of an internal counterion in the phospholipid, a preferred counterion is a monovalent cation such as sodium ion. The phospholipid may be salted or desalted, hydrogenated, or partially hydrogenated. The phospholipid surface active substance can be a mixture of these phospholipids.

Preferred phospholipids include Lipoid E80, Lipoid EPC, Lipoid SPC, DMPG, Phospholipon 100H, a hydrogenated soybean phosphatidylcholine, Phospholipon 90H, Lipoid SPC-3, egg phospholipid, purified egg phospholipid, and mixtures thereof. A currently most preferred phospholipid is Lipoid E80.

The concentration of surface active substance added to the formulations prepared according to this invention can be present in the range of 0.1 to 50%, preferably 0.2 to 20%, and more preferably 0.4 to 15%. A currently preferred level of Lipoid E80 is from about 0.4% to 15%, more preferably from about 0.5% to about 10%, and most preferably from 2 to 5%.

In a preferred aspect, a process is provided for the preparation of small particles containing fenofibrate and a phospholipid surface stabilizing substance which comprises the steps of (a) mixing at high shear an admixture of the poorly water-soluble drug and a phospholipid substance in an aqueous carrier in the absence of an organic solvent and optionally in the presence of one or more than one surface active substances within a first temperature range at or above the melting point of the drug to form a heated suspension containing the drug, then (b) homogenizing said heated suspension in a first pressure range and within said first temperature range to form a heated homogenate containing the drug, then (c) cooling said heated homogenate to a second temperature range below the melting temperature of the drug to form a transiently stable cooled homogenate containing the drug, then (d) applying a particle stabilizing energetic process to said cooled homogenate within a second temperature range and in a second pressure range to form a cooled dispersion of stabilized small particles containing the drug, and then (e) optionally drying the cooled dispersion to form dried small particles containing the drug. A statin can be added at any of the above steps, but is preferably added at some point after cooling of the heated homogrenate.

In a specific aspect, the present invention is directed to a composition and a process for the preparation of microparticles of fenofibrate, which small particles are used to prepare an orally administered pharmaceutical composition comprising said microparticles of solid fenofibrate and a statin that are stabilized b a phospholipid surface active substance, wherein said microparticles are prepared in the presence of said phospholipid surface active substance, and wherein a therapeutically effective amount of said composition provides a quantity of fenofibrate to a fasted human patient in need of treatment that is greater than 80% of the quantity of fenofibrate provided by said amount to said patient when fed at least 1000 calories 50% of which are from fat.

The process comprises the steps of (a) mixing at high shear an admixture of the poorly water-soluble drug fenofibrate and a phospholipid substance in an aqueous carrier in the absence of an organic solvent and optionally in the presence of one or more than one surface active substances within a first temperature range at or above the melting point of the drug to form a heated suspension containing the drug, then (b) homogenizing said heated suspension in a first pressure range and within said first temperature range to form a heated homogenate containing the drug, then (c) cooling said heated homogenate to a second temperature range below the melting temperature of the drug to form a transiently stable cooled homogenate containing the drug, then (d) adding a desired amount of a statin to the cooled homogenate, then (e) applying a particle stabilizing energetic process to said cooled homogenate within a second temperature range and, in a second pressure range to form a cooled dispersion of stabilized small particles containing both drugs, and then (f) optionally drying the cooled dispersion to form dried matrix containing both drugs.

An admixture of a poorly water-soluble fibrate and a surface active substance such as a phospholipid substance can be prepared by adding a surface active substance and the poorly water-soluble fibrate to an aqueous carrier and then mixing at high shear, for example for up to 30 minutes at a shear rate of up to 10,000 rpm. As an example, an admixture of fenofibrate and a phospholipid substance can be prepared by adding a phospholipid substance and fenofibrate to an aqueous carrier and then mixing the admixture at high shear for up to 30 minutes at a shear rate of up to 10,000 rpm. Preferably the fenofibrate used to form the admixture is in the form of a powder or small crystals or small pieces that are less than about 5 mm in diameter to facilitate mixing. Larger sized crystals or masses of drug can be milled to about 5 mm or smaller before forming the admixture used in this invention to facilitate mixing.

Suitable aqueous carriers include water, sterile water, water for injection, and buffered water such as phosphate buffered water. The pH of the buffer can be in the range of from 4 to 10, preferably from 7 to 9, and most preferably from 7.5 to 8.5. A preferred aqueous carrier is 0.01 to 10 mM sodium phosphate buffer. The pH of the carrier is preferably established at room temperature before mixing with the phospholipid substance and the poorly water-soluble drug and before heating to a first temperature. The pH may be adjusted by addition of an acid or base such as HCl or NaOH to a solution of a phosphate salt. Preferably the aqueous carrier contains no dissolved oxygen. A currently most preferred aqueous carrier is 10 mM phosphate buffer. Optionally, one or more carbohydrates or bulking agents can be added to the aqueous carrier. Preferred carbohydrates and bulking agents include monosaccharides, disaccharides, trisaccharides, and sugars such as sucrose, raffinose, lactose, mannitol, sorbitol, trehalose, glycerol, dextrose, fructose, a pentose, a hexose, xylitol, and mixtures thereof. Most preferred carbohydrates and bulking agents include sucrose, raffinose, sorbitol, trehalose, and mixtures thereof. Concentrations of the carbohydrates can range from about 5% to about 40%, preferably about 10% to about 30%.

When raffinose is used in the compositions of this invention, it is preferably used together with sucrose with the ratio of sucrose to raffinose in the range of about 1:1 to about 500:1, more preferably in the range from 10:1 to 100:1.

In one aspect, the aqueous carrier can initially be at a temperature between about 4° C. to about 100° C., preferably between 20° C. and 90° C., and more preferably between 20° C. and 50° C. This is particularly useful for fenofibrate. The aqueous carrier can be heated to the desired first temperature range before or after the addition of the admixture.

In another aspect, the aqueous carrier can be heated to a temperature higher than 100° C., for example superheated up to 275° C. In this case, the aqueous carrier can be contained in a closed vessel or apparatus at a pressure higher than ambient pressure. The superheated aqueous carrier and the admixture can be contained in a pressurized closed system such as a stainless steel vessel in which high speed shear can be applied. The vessel is preferably connected through suitable piping and valves to a heated homogenization apparatus which further comprises a reservoir and optionally a return pipe that can carry homogenate from the homogenizer back to the vessel if used in a continuous or batch-wise mode. The vapor pressure of water at 100° C. is approximately 14.7 psi and it rises as the temperature is increased. For example, at 120° C. the vapor pressure of water is approximately 28.8 psi; at 140° C. it is approximately 52.4 psi; at 160° C. it is approximately 89.6 psi; at 180° C. it is approximately 145.4 psi; at 200° C. it is approximately 225.5 psi: at 220° C. it is approximately 337 psi; at 240° C. it is approximately 486 psi; at 260° C. it is approximately 680 psi; and at 275° C. it is approximately 863 psi. A closed system useful in this invention can safely contain the heated components of this invention at least at these and higher pressures and temperatures and used to provide small particles of poorly water-soluble drug according to this invention.

After the poorly water-soluble drug and surface active substance such as fenofibrate and a phospholipid substance are added to the aqueous carrier, the admixture can then be heated if not already so, preferably in the absence of oxygen such as under a nitrogen or argon atmosphere, until the temperature rises to a first temperature range that is at or above the melting point of the drug. In the case of fenofibrate the admixture in the aqueous carrier can be heated to between 79° C. (the reported lowest melting point of fenofibrate) and 99° C., preferably between 79° C. and 95° C. and most preferably between 80° C. and 90° C. In general it is preferred that the temperature is at or up to about 20° C. above the melting point of the drug. Thus, the preferred first temperature range is in general from the melting point of the drug to about 20° C. above the melting point of the drug. The aqueous carrier can be heated to the first temperature range before or after the addition of the drug and the surface active substance. The admixture is maintained at the first temperature range while high shear mixing is applied. The admixture when thus prepared comprises a crude emulsion of melted drug and surface active substance in the heated aqueous carrier.

During the heating of the admixture, high shear mixing is applied. Suitable shear is derived for example from propeller-containing mixers, homogenizers, blenders, sonicators or other devices capable of producing a heated suspension. Suitable shear rates can range between 500 to 10,000 rpm. preferable 2,000 to 5,000 rpm. High shear mixing can be continued for up to 30 minutes or even longer if needed to form a heated suspension containing the drug. High shear mixing of the admixture when the temperature is below the melting point of the drug provides a suspension of the admixture in the aqueous carrier, and such suspension is useful as an antecedent to the heated suspension that is produced when the temperature is increased to or above the melting point of the drug. Continued application of high shear mixing or application of more vigorous or ultra-high shear mixing when the temperature is above the melting point of the drug can produce a heated homogenate of the admixture in the aqueous carrier. When the temperature is above the melting point of the drug, the heated suspension is a suspension of melted drug and surface active substance in the aqueous carrier. In one aspect, the heated suspension is an emulsion of melted drug and surface active substance in the aqueous carrier. High shear mixing and ultra-high shear mixing can be produced by the input of mechanical energy for example using a mechanical mixer or stirrer or mill configured with a mixing blade or propeller that can induce efficient mixing and particle size reduction through high shear turbulence, turbulent eddies, transfer of high fluid kinetic energy, high energy dissipation, pressure induced cavitation, and similar known mechanisms of homogenization.

In one aspect, devices useful in the preparation of a heated suspension of this invention can be employed in the preparation of the heated homogenate of this invention if sufficient energy is transferred to the particles of the heated suspension to produce a heated homogenate. In this case, heating of the admixture to form a heated suspension and then homogenization of the heated suspension to form a heated homogenate can be done as a continuous step combining step (a) and step (b) into a single step wherein a heated suspension is formed and then converted into a heated homogenate without substantial change in apparatus or without substantial increase in energy applied to the heated admixture formulation.

As used herein, homogenization refers to the creation of a homogenate or uniform distribution of small particles containing drug in an aqueous carrier as a result of an energetic process being applied to an antecedent composition such as a mixture, admixture, blend, emulsion, suspension, dispersion or other composition of solids or solid particles or liquids or liquid particles or droplets comprising drug and one or more than one surface active substance in an aqueous carrier wherein the homogenate and the small particles produced are at least transiently stable toward phase separation into larger particles or droplets or non-uniform solid or liquid domains. Homogenization, particularly with respect to the formation of a heated suspension and a heated homogenate, can be achieved by input of mechanical energy such as by high shear mixing, ultra high shear mixing, high speed blending, microfluidization, and milling such as by dispersion milling, ball milling, attrition milling, vibrator milling, and media milling, or by application of sonic energy in the form of sonication. Preferably in the case of a mill being used in this process wherein the mill contains media or grinding media, such media is removed in a filtration or other suitable separation process to provide homogenized compositions of this invention. Homogenization is preferably achieved by passing an antecedent composition Linder high pressure, for example under more than 1000 psi, through a tiny orifice which can result in a decrease in the average diameter and an increase in the number and surface area of particles or droplets in the antecedent composition and produce small particles. A preferred homogenization method comprises passing an antecedent composition under high pressure through a tiny orifice and includes microfluidization. particularly with respect to homogenization to prepare a cooled dispersion of this invention.

The drug can be added to the aqueous carrier as a solid. Preferably for example the drug such as fenofibrate can be added in the form of particles ranging in size up to about 10 mm such as milled or micronized particles or powders. Milled particles can be obtained for example by air jet milling of bulk powdered or crystalline fenofibrate. The drug can also be added to the aqueous carrier as a molten material, i.e., heated at or above its melting point, preferably at the melting point of the drug to about 20° C. above the melting point of the drug but at a temperature less than its decomposition point. For fenofibrate the preferred temperature can be from about 80° C., the melting point of the drug, to about 100° C. although temperatures up to the decomposition point of the drug are also suitable.

The concentration of the surface active substance in the aqueous carrier can vary between 0.1% w/w and 90% w/w, preferably between 0.1% w/w and 50% w/w, and more preferably between 0.1% and 20%, and most preferably between 0.5% to 10% w/w. The concentration of the drug such as fenofibrate in the aqueous carrier can vary between 0.1% w/w and 90% w/w, preferably between 0.5% w/w and 50% w/w, and more preferably between 1% and 20% w/w. For example, in one aspect a currently preferred composition comprises 3% to 10% of a phospholipid substance as a surface active substance and 14% of the poorly water-soluble drug fenofibrate in 10 mM phosphate buffer at pH 8 as an aqueous carrier. In another aspect, a currently preferred composition comprises about 0.5% of a phospholipid substance as a surface active substance and about 10 to 14% of fenofibrate.

The surface active substance can be added to the aqueous carrier at any temperature below its decomposition point. When used as a mixture of surface active substances, the individual components can be added separately to the aqueous carrier or combined as mixtures before addition. The surface active substance can be added together with the drug, for example with fenofibrate or separately to the aqueous carrier.

The admixture of the drug, for example fenofibrate, and a surface active substance such as a phospholipid substance in an aqueous carrier is heated to a first temperature range during the application of a high shear mixing to produce a heated suspension containing the drug.

The heated suspension containing the drug is then homogenized at the first temperature range to form a heated homogenate. The first temperature range is maintained during this homogenization to ensure that the drug is maintained in a molten state. For fenofibrate, the first temperature range is preferably from 80° C. to 100° C. and more preferably from 80° C. to 90° C. provided that fenofibrate remains molten.

Homogenization of the heated suspension containing the drug can be carried out in equipment suitable for that process. Useful equipment includes commercially available high pressure homogenization equipment such as APV Gaulin M15, Avestin Emulsiflex C5 or C50, and MFIC Microfluidizer M110EH and other commercially available microfluidizers and commercially available microfluidizers modified to accommodate heat exchangers and temperature monitoring devices and piping and valves to carry heated suspensions or emulsions. The microfluidizers can be heated to the first temperature range, for example by use of electrical resistance, heated air bath, or heated fluid bath such as a water or silicone oil bath heated to the first temperature range that is at or above the melting point of the drug.

Homogenization of the heated suspension containing the drug is done at a first pressure range in the homogenization chamber of a heated homogenization apparatus while the drug is maintained in its molten state. The first pressure range can be from 2,000 psi to 30,000 psi, preferably about 5,000 psi to 20,000 psi, and more preferably from about 3,000 psi to about 10,000 psi.

The heated suspension containing the drug can be processed into the homogenization chamber of the homogenization apparatus by gravity feed from a heated and optionally stirred reservoir or by aid of a pump, for example a peristaltic pump, from a reservoir heated to the first temperature range through the heated homogenization chamber of the heated homogenizer and thence into a heated receiving vessel heated to the first temperature range in such a manner as to ensure the entire fluid volume of the heated suspension is subjected to discrete homogenization resulting in a homogeneous suspension of heated submicron or micron molten particles. In one aspect of this invention, between each homogenization pass the processed heated suspension is returned batch-wise from the heated receiving vessel back into the heated reservoir such as by means of a pump or by pouring, and the heated homogenization step is repeated. In another aspect, the processed heated suspension is fed directly back into the heated reservoir in a continuous process. If the aqueous carrier is heated above 100° C., the system is contained as a closed system under pressure during the feeding of the admixture to the homogenization apparatus and during the return of the homogenized or partially or not-completely homogenized heated suspension to the heated reservoir. If the initial volume of the heated suspension before homogenization is defined as a volume pass, then the number of volume passes made through the homogenizer in this manner can range from one to about 20, preferably from one to ten, more preferably from 2 to 8, and most preferably from 4 to 7 to produce a heated homogenate that is initially at the first temperature range at or above the melting point of the drug. A preferred drug in this process is fenofibrate which has a preferred first temperature range of from 80° C. to about 100° C. and more preferred from 80° C. to about 90° C.

While it is not known with certainty, it is appreciated that forcing a drug and a surface active substance such as a phospholipid under conditions of elevated pressure and temperature through a microfluidizing chamber can cause transient gradients in temperature, the microfluidization process being exothermic and causing a rise in the temperature of the processed suspension of particles or emulsions during particle size reduction. While the transient rise in temperature is usually controlled by a temperature regulating device such as a heat exchanger, it is possible that transient concentration gradients of poorly water-soluble drug and stabilizer are established or continue to exist in the rapidly moving non-equilibrium state of the microfluidizer. Water insoluble or poorly soluble components of the formulation (e.g., fenofibrate and phospholipid) may be forced into solution temporarily, perhaps at a molecular level thereby creating a supersaturated or molecularly distorted environment which if left undisturbed will subsequently achieve equilibrium again. It is postulated that transient concentration gradients may be established in the microfluidization process wherein molecules of drug and stabilizer are forced into an aqueous environment to give a transiently stable but novel composition and non-equilibrium condition. It is expected that this novel composition will not be achieved if the microfluidization is carried out on solid fenofibrate at a lower temperature, and a different composition will obtain in that case.

We have found that this heated homogenate can be cooled to a transiently stable or metastable cooled homogenate. By metastable stable we mean that upon agitation or long-term standing the transiently stable particles of the cooled homogenate will convert to larger particles of crystallized or precipitated drug and can demonstrate phase separation of components of the homogenate from the aqueous carrier. For example, under these conditions fenofibrate forms a transiently stable or metastable cooled homogenate that on standing or application of manual agitation such as shaking or stirring produces larger crystals. However, we have surprisingly found that the lifetime of the transiently stable particles of the cooled homogenate can be moderately extended by control of cooling conditions. Additional prolonged stability of the small particles can be obtained by subsequent homogenization at a second temperature range that is below the melting point of the drug. We have also found that the total number of homogenization volume passes used in the heated and cooled homogenization processes of this invention is substantially fewer than the number of volume passes needed to produce an approximately comparable drug suspension starting from the powdered or micronized drug that was used to prepared the admixture in this invention but homogenized while the drug was maintained entirely in the solid state according to prior art methods.

In one aspect the average particle size of the heated homogenate can be measured using a laser light diffraction based instrument such as a Malvern Mastersizer Microplus and shown to be less than one micrometer. However, if an attempt is made to collect and keep the heated homogenate in a receiving vessel that is not preheated to the first temperature, a poorly water-soluble drug such as fenofibrate immediately precipitates from the heated homogenate as a solid, and in the case of fenofibrate as crystals. This is very likely related to agitation of the transiently stable dispersion.

In the case of fenofibrate, microscopic examination of a heated homogenate shows it to be comprised of small and non-crystalline particles in suspension, but there is a tendency for fenofibrate to crystallize out on the microscope slide. This rapid crystallization is also seen if the heated homogenate is collected in a receiver at ambient temperature.

A transiently stable or metastable cooled homogenate can be obtained from a heated homogenate derived from an admixture of drug and a surface active substance such as a phospholipid substance in an aqueous carrier by rapidly cooling the heated homogenate under non-agitating conditions from a first temperature range at or above the melting temperature of the drug to a second temperature range below the melting point of the drug, preferable to the range of 1° C. to about 20° C. In some cases, depending on how readily the drug crystallizes, under non-stirred conditions the cooled homogenate can retain small non-crystalline particles very similar to those detected initially in the heated homogenate.

Optionally, the heated homogenate can be held at the first temperature range that is above the melting point of the drug, for a holding time before the onset of cooling to the second temperature range. Agitation during the holding period above the melting point of the drug does not effect crystallization of the drug. However, agitation such as by stirring of the cooled homogenate can induce growth in particle size and crystallization and precipitation of drug.

In particular, in the case of fenofibrate we have found that a transiently stable or metastable cooled homogenate can be obtained from a heated homogenate derived from an admixture of fenofibrate and a phospholipid substance in an aqueous carrier by rapidly cooling the heated homogenate under non-agitating conditions from a first temperature range at or above the melting temperature of fenofibrate to a second temperature range below the melting point of fenofibrate, preferably to the range of 1° C. to about 40° C., more preferably from about 4° C. to about 40° C. and fenofibrate is not molten. Under non-stirred conditions the cooled homogenate retains small non-crystalline particles very similar to those detected initially in the heated homogenate. Optionally, the heated homogenate can be held at the first temperature range, for example at 80° C. to 90° C., for a holding time before the onset of cooling to the second temperature range. Agitation during the holding period does not effect crystallization of the fenofibrate.

To determine a minimum holding time at 80 to 90° C. before the induction of cooling for a fenofibrate-containing heated homogenate, the holding time was varied at 15 minute intervals from 0 to 60 minutes and a cooling period in a bath held at 5° C. was kept constant at 30 minutes after the onset of cooling. In these experiments we find that particle mean diameters of the cooled homogenate are similar under all conditions studied. Thus, samples of freshly prepared heated homogenate can be held at a first temperature range for a holding period or they can be immediately cooled to a second temperature range after completion of the first homogenization step.

A number of cooling methods can be applied to the heated homogenate containing a poorly water-soluble drug to cool it from the first temperature range at or above the melting point of the drug to a temperature below the melting point of the drug to form a cooled homogenate. Examples of several methods are listed and illustrated with respect to fenofibrate as follows.

Method 1: slow cooling in ambient air optionally in a closed vessel that excludes oxygen and air by allowing the heated homogenate to stand unagitated and to cool from above the melting point of the drug to ambient room temperature;

Method 2: slow unagitated cooling from above the melting point of the drug which for fenofibrate is about 85° C. in a water bath at ambient temperature which is approximately 15° C. to 20° C;

Method 3: slow stepwise cooling at 1 degree Centigrade per minute in a stirred oil bath from above the melting point of the drug to ambient temperature;

Method 4: slow stepwise cooling from above the melting point of the drug to about 20° C. below the melting point of the drug which for fenofibrate is from about 85° C. down to 65° C., followed by cooling to 4° C. in an isothermally cooled 4° C. water bath;

Method 5: fast cooling in an isothermally cooled 4° C. water bath;

Method 6: slow stepwise cooling from above the melting point of the drug to about 40° C. below the melting point of the drug which for fenofibrate is from about 85° C. to about 40° C. at the rate of 1 Centigrade degree per minute.

For cooling from temperatures initially above 100° C. the heated homogenate is maintained in a pressurized vessel. After cooling, the pressure can then be optionally adjusted to ambient without agitation of the contents of the vessel typically by means of a valve that permits pressure equalization to ambient pressure conditions. Preferably an inert atmosphere such as a nitrogen or argon atmosphere is maintained in contact with the formulations of this invention.

The effect of stirring during the cooling phase was examined for fenofibrate as an example. In some studies, samples were left unagitated while others were stirred magnetically at 250 rpm using Teflon-coated magnetic stirring bars during cooling methods. Additionally, in some experiments, heated homogenate was diluted ten fold with additional aqueous carrier that had been heated to the first temperature, the diluted heated homogenate was then swirled to evenly distribute the added aqueous carrier, and then the diluted heated homogenate was cooled.

Particle size determinations were carried out using a Malvern Microplus Mastersizer. Samples were examined at two to three hours after the initiation of cooling. Results are reported as volume weighted averages or D(4,3). Samples were also examined microscopically under bright polarized light using both in-phase and out-of-phase modes. In-phase light allowed determination of the primary particle size and the detection of aggregates. Out-of-phase examination gave an indication of the amount of crystals formed in the composition. Morphologically small crystalline particles of fenofibrate were easily distinguished from large fenofibrate crystals.

When 3% Lipoid E80 (also sometimes referred to as E80 herein below) was used as a phospholipid substance in a single pass homogenization preparation of a heated homogenate containing 10% fenofibrate, little difference was observed in the particle characteristics when cooled by either method 1 or 2 (average particle size at 3 hours was 2.42 and 2.96 micrometers, respectively). The particles were initially non-crystalline, spherical and submicron but crystals appeared within 3 hours. In contrast, when 3% Lipoid E80 was used as a phospholipid substance in a two pass homogenization preparation of a heated homogenate containing 10% fenofibrate, a smaller particle size was unexpectedly observed when a sample was cooled by method 1 versus when a sample was cooled by method 2 (0.56 and 1.64 micrometers, respectively after 3 hours of cooling). This difference was different from that seen in heated homogenates prepared with saturated lipids such as phospholipon 100H (also sometimes referred to as 100H herein below) and phospholipon 90H (also sometimes referred to as 90H herein below) when processed for two passes. In these formulations, the particle size at 2 to 3 hours after initiation of cooling was significantly higher than that seen using Lipoid E80. For heated homogenates prepared using 3% phospholipon 100H in two passes and cooled for 3 hours according to methods 1 and 2, the average particle sizes were 14.72 and 10.31 micrometers, respectively. For heated homogenates prepared using 3% phospholipon 90H in two passes and cooled for 2 hours according to methods 1 and 2, the average particle sizes were 6.07 and 5.23 micrometers. respectively. Microscopically the cooled homogenates containing phospholipon 100H and phospholipon 90H consisted of particle aggregates with crystals appearing over time. Aggregates were not typically seen in Lipoid E80 formulations but crystal growth occurred over time.

It was unexpectedly found that increasing the cooling rate in the absence of agitation produced cooled homogenates that maintained small particles containing the poorly water-soluble drug fenofibrate to a greater degree than those produced by slow cooling methods. This was especially true when Lipoid E80 was used as the phospholipid substance. For example, when a sample of heated homogenate prepared from 3% Lipoid E80 as the surface active substance and 10% fenofibrate in two homogenization passes was cooled by method 5 (fast cooling) and compared to a cooled sample of heated homogenate of the same composition cooled according to methods 1 or 2 (slow cooling), the particle size at 3 hours for fast cooling was 0.63 micrometers versus 0.76 micrometers for slow cooling.

For non-stirred samples, minimal particle size increases can be observed in all cooling methods while under stirred conditions substantial crystallization or precipitation or agglomeration of poorly water-soluble drug can be observed. For example, for non-stirred samples containing fenofibrate, minimal particle size increases were observed in all cooling methods. In contrast, under stirred conditions substantial crystallization of fenofibrate was observed for all cooling methods. For sample cooled in a slow step process, crystal growth occurred at temperatures lower than about 20° C. below the melting point of the drug, i.e., for fenofibrate below about 60° C.

It can be seen that energy imparted to the cooled homogenate by mechanical stirring for example using a stirring bar or spatula is not sufficient to impart stability to the particles of the cooled homogenate. To be effective, a particle stabilizing energetic process must impart sufficient energy to the particles of the cooled homogenate to convert them from a transiently stable homogenate into a longer lived dispersion of particles. Otherwise, undesirably large particles will be produced from the transiently stable cooled homogenate. Preferred particle stabilizing energetic processes include sonication, homogenization and microfluidization. A most preferred particle stabilizing energetic process is homogenization. It is believed that enough energy must be applied to the particles to modify some aspect of the particle composition which, while currently unknown, may be related to further reduction in particle size in the presence of a surface active substance or reorganization of drug and/or surface active substance molecules at or on the surface of the particle, or other phenomena.

Oral formulations of fenofibrate microparticles stabilized by phospholipid surface active substance and prepared by homogenization or microfluidization or hot melt homogenization or sonication provide unexpected reduction in food effect on the uptake of fenofibrate between fasted and fed conditions.

Diluting the heated homogenate ten fold with additional heated aqueous carrier was found unexpectedly to have a beneficial effect on the size of particles when cooled. Results for fenofibrate as an example are displayed in Table 1. Attention is drawn to the bottom two rows of Table 1 which show that the particle size of diluted suspension of fenofibrate is smaller than that of undiluted suspension

TABLE 1

Effect of dilution with aqueous carrier on cooled particle sizes in micrometers of heated homogenate containing 10% fenofibrate and 3% phospholipid

| Phospholipid (one pass) | E80 | E80 | 100H | 100H | 90H | 90H |
|---|---|---|---|---|---|---|
| Cooling method (time of cooling) | 1 (3 h) | 2 (3 h) | 1 (3 h) | 2 (3 h) | 1 (2 h) | 2 (2 h) |
| Undiluted average particle size | 2.42 | 2.96 | 11.46 | 9.71 | 4.83 | 4.12 |
| Diluted average particle size | 1.84 | 1.69 | 3.29 | 3.77 | 2.17 | 2.73 |

Cooled homogenate having average particle size of less than 1 micrometer can usually be achieved by subjecting the heated homogenate containing melted drug to multiple homogenization passes prior to rapid cooling. The effect of multiple homogenization is to produce smaller particles, but the size reducing effect is non-linear and shows decreasing rates of return, i.e., the average particle size decreases non-linearly with an increasing number of passes.

In the case of fenofibrate, it was also found that increasing the number of heated homogenization passes from one to two followed by cooling produced a cooled homogenate with smaller particle size with Lipoid E80 but not with Phospholipon 100H or Phospholipon 90H. For example, at 3 hours after cooling, a cooled homogenate sample containing fenofibrate prepared according to method 1 had a particle size of 0.56 micrometers when the antecedent heated homogenate had been subjected to two passes of homogenization compared to a particle size of 2.42 micrometers when the antecedent heated homogenate had been subjected to one homogenization pass. When a heated homogenate had been subjected to 10 homogenization passes, the cooled homogenate had a particle size of 0.29 micrometers. It was generally found that cooled homogenate having particle size of about 0.3 micrometers could be achieved from heated homogenate that had been subjected to at least 5 homogenization passes. Additional homogenization produced smaller particles, but at decreasing rates per volume pass. For examples, particles as small as 0.1 micrometers can be achieved under homogenization conditions. Results for one and two homogenization volume passes as a function of phospholipid are displaced in Table 2.

TABLE 2

Difference between one and two heated homogenization passes on cooled particle sizes in micrometers of heated homogenates containing 10% fenofibrate and 3% phospholipid

| Phospholipid | E80 | E80 | 100H | 100H | 90H | 90H |
|---|---|---|---|---|---|---|
| Cooling method (time of cooling) | 1 (3 h) | 2 (3 h) | 1 (3 h) | 2 (3 h) | 1 (2 h) | 2 (2 h) |
| One pass average particle size | 2.42 | 2.96 | 11.46 | 9.71 | 4.83 | 4.12 |
| Two pass average particle size | 0.56 | 1.64 | 14.72 | 10.31 | 6.07 | 5.23 |

We have also found that the pass dependent particle size of the cooled homogenate can be a function of the ratio of the concentration of surface active substance to drug. For example, a heated homogenate prepared using 3% Lipoid E80 as the surface active substance and 10% fenofibrate as the drug and subjected to 10 homogenization passes produced a cooled homogenate by method 6 that had a particle size of 0.35 micrometers while a heated homogenate prepared using 10% Lipoid E80 as the surface active substance and 10% fenofibrate as the drug and subjected to 10 homogenization passes produced a cooled homogenate by method 6 that had a particle size of 1.3 micrometers.

Furthermore, when a heated homogenate was prepared using 3% Phospholipon 100H as the surface active substance and 10% fenofibrate as the drug, subjected to 10 homogenization passes and cooled, a cooled homogenate was produced by method 5 that had a particle size of 1.45 micrometers. In comparison, when a heated homogenate wNas prepared using 3% Lipoid E80 as the surface active substance and 10% fenofibrate as the drug, subjected to 10 homogenization passes and cooled, a cooled homogenate was produced that had a particle size of 1.3 micrometers.

Fast cooling of heated homogenates in a 4° C. bath under non-stirred conditions produces cooled homogenates with minimum change in morphology and particle size from that observed in the heated homogenates prior to cooling. For example, we have discovered that fast cooling of heated homogenates containing a phospholipid as the surface active substance and fenofibrate as the drug in a 4° C. bath under non-stirred conditions produced non-crystalline cooled homogenates with minimum change in morphology and particle size from that observed in the heated homogenates prior to cooling. When samples of heated homogenate were held at 80° C. for up to one hour and then cooled to form cooled homogenates that were held for 30 minutes at 5° C., no differences in particle size could be detected as a function of the time the heated homogenate was held at 80° C. before cooling. For optimum processing speed, freshly prepared samples of heated homogenate can be cooled from the first temperature range to a second temperature range immediately after an adequate number of homogenization passes such as five passes of heated homogenation to provide cooled homogenates. However, cooled homogenates thus prepared appear to be transiently stable or metastable toward formation of crystals of drug that can grow larger and precipitate from the suspension of the cooled homogenate if allowed to stand. The formation of larger particles and crystals is enhanced if the cooled homogenate is disturbed such as by stirring or shaking.

Preferably, the average particle size of the microparticles of fenofibrate stabilized with phospholipid is less than 10 microns, more preferable less than 5 microns, even more preferably less than 4 microns, yet even more preferably less than 3 microns, yet even more preferably less than 2 microns, and most preferably less than 1 micron. Microparticles that are less than about 0.5 microns are especially preferred.

In another aspect of this invention, bulking agents or bulking agent excipients (i.e., pharmaceutically acceptable excipients including those used in currently available formulations of fibrates alone and of statins alone) can be added as solids or in solutions of aqueous carrier at steps in the current procedure. Preferably soluble sugars can be added to the admixture of drug and a surface active substance in an aqueous carrier in the process of this invention.

A bulking agent is herein defined as a compound, usually a pharmaceutically acceptable excipient, useful in assisting redispersion of dried small particles back into a suspension such as an aqueous suspension. Suitable bulking agents include hydroxyl-containing, hydrophilic, relatively low molecular weight (less than 50,000) compounds such as sugars, including monosaccharides, disaccharides, trisaccharides, sucrose, raffinose, lactose, mannitol, sorbitol, trehalose, glycerol, dextrose, fructose, pentoses, hexoses, xylitol, and mixtures thereof. Bulking agents are useful as protectants in a drying process such as cryoprotectants in a lyophilization process or as additives in a spray drying process or an evaporation process, preventing or substantially reducing particle fusion, combination, suspension degradation and agglomeration during drying, and assisting in the resuspension of particles from a dried state to form a suspension of the particles. Dry small particles containing a poorly water-soluble drug can be produced for example as a lyophilizate which is a solid produced from a cooled dispersion of particles by the process of freezing the aqueous carrier to a solid comprising a dispersion in ice and then removing the water by subliming the ice under reduced pressure. Bulking agents can also reduce or depress the freezing, point of aqueous compositions in which they are dissolved or partially dissolved.

Bulking agents can be added in amounts from 0.1% to about 60% w/w or more depending on the intended use. Additional amounts of bulking agents can be added to the phospholipid-stabilized microparticles after they have been prepared as a suspension, for example prior to a drying step such as a spray drying step or a lyophilization step, or after they have been dried or substantially dried. Mixing of bulking agents with dried or substantially dried microparticles can be done by mixing the ingredients or by adding one or more bulking agents to the microparticles or vice versa and subsequently blending the ingredients. Alternatively, the microparticles can be resuspended in a liquid or fluid such as an aqueous fluid and admixed with bulking agents as solutions, suspensions, or as dried substances, and the liquid or fluid can be subsequently removed. Depending on the intended use and ultimate formulation and dosage form, bulking agents such as monosaccharides, disaccharides, trisaccharides, sucrose, raffinose, lactose, mannitol, sorbitol, trehalose, glycerol, dextrose, fructose, pentoses, hexoses, xylitol, and mixtures thereof can be added in amounts varying from about 0.1% up to their solubility limits in solution. Additional quantities can be added by blending of dried microparticles plus bulking agents with additional bulking agents. A preferred range of these ingredients is such to provide from about 1% to about 90% of a tablet or capsule dosage form.

In yet another aspect of this invention, the phospholipid-stabilized microparticles can be sprayed onto the surface of a bulking agent. For example, if the bulking agent is in the form of a particle or bead, preferably in the range of about 5 micrometers to about 0.5 millimeters or even up to about 2 mm in some cases, of a pharmaceutically acceptable material or excipient, a suspension of phospholipid-stabilized microparticles optionally containing additional dissolved or suspended bulking agent (which can be the same composition as the particle or bead or a different composition from the material in the particle or bead) can be spray coated onto the surface of the bulking agent particle or bead to create a layer and optionally a multilayer derived from repetitive spray coating. For example, a combination of a statin and fenofibrate microparticles stabilized by a phospholipid in an aqueous suspension of a sugar such as sucrose can be sprayed onto the surface of a sugar bead or particle such as a sucrose bead or a lactose bead or a starch bead or a polyvinylpyrrolidone or PVP bead in a single layer or in multiple layers, and the coated beads so produced can be optionally mixed with pharmaceutically acceptable excipients and placed in capsules or compressed into tablets or maintained as powders to provide dosage forms of this invention.

Currently preferred bulking agents include trehalose, sucrose, raffinose, sorbitol, and mixtures thereof. Preferred levels of these bulking agents in the admixture range from about 1% to about 40% w/w, and more preferably from about 2% to about 30% w/w.

The combination of statin and phospholipid-stabilized microparticles that exhibit a substantial reduction in food effect as described in this invention can be employed in a number of dosage forms including tablets, capsules, and powders, which powders can be dispersed in a beverage such as a citrus beverage (e.g., orange juice and the like) or a food beverage such as a vegetable juice, or a flavored beverage sometimes used by a patient on a restricted calorie diet or a restricted fat diet such as Slim-Fast™ and similar beverages. Particularly useful also are the dosage forms disclosed in WO 00/30616, the contents of which is hereby incorporated by reference.

Bulking agents can be added to the admixture, to the heated suspension, to the heated homogenate, to the cooled homogenate to the cooled dispersion, and to the dried particles. They can be added as solids, as liquids, as solutions in aqueous carrier when soluble therein, or in combinations thereof. In one embodiment, bulking agents added to a composition such as a cooled homogenate and the like as part of this invention are preferably soluble in the aqueous suspension rather than only swellable therein when the composition plus bulking agent is to undergo an additional homogenization step with a microfluidizer.

The stability of cooled homogenate formulations with respect to the effect of addition of a bulking agent (or a pharmaceutically acceptable excipient) or a combination of excipients was examined. When bulking agents were added as solids or liquids to heated admixtures of fenofibrate and a phospholipid substance as a surface active substance in an aqueous carrier, then processed for example using 10 heated homogenization passes at 80° C. and subsequently cooled in a 4° C. water bath, particle size estimates suggested that with the exception of the bulking agent sucrose (10%), there was little increase in particle mean diameter measurements over a 2 h period. However microscopic observations revealed the presence of a significant number of large crystals after the cooling step. Addition of 2-fold hot buffer solution containing either nothing or bulking agents to the processed formulations, caused a large increase in the mean particle diameter. This was attributed by microscopic examination to be due to particle aggregation together with large crystals also present.

When trehalose was added to an admixture of fenofibrate and a phospholipid substance in an aqueous carrier, on stirring crystals were detected indicating that trehalose did not stabilize these metastable formulations with respect to crystal formation and precipitation. PVP 17 and glycerol were added to heated homogenates, and in both cases crystal growth was observed microscopically under stirred conditions. When glycerol alone or glycerol and trehalose were added to the admixture and then homogenized, results from stirring experiments again showed that these formulations were unstable with extensive crystallization observed over time. Thus, adding bulking agents or PVP to either the admixture or to the heated homogenate does not result in stabilization of the metastable formulation under stirring conditions.

Whereas a cooled homogenate can be unstable with respect to agitation such as stirring or manual shaking, we have surprisingly found that a cooled homogenate can be transformed into a more stable cooled dispersion by application of a particle stabilizing energetic process applied at the second temperature range and in a second pressure range.

For example, although the aforementioned cooled homogenates of fenofibrate were found to be unstable with respect to agitation such as stirring or manual shaking that lead to the formation of crystals of fenofibrate, we have found that the cooled homogenate can be transformed into a more stable cooled dispersion by application of a particle stabilizing energetic process applied at the second temperature range and in a second pressure range.

Examples of suitable particle stabilizing energetic processes include homogenization, microfluidization, and sonication. Microfluidization is generally considered to be a method of homogenization. Microfluidization of fenofibrate in the presence of a phospholipid stabilizing agent produces a novel composition that when formulated into a suitable dosage form such as a tablet or capsule as a dried solid optionally in the presence of one or more excipients such as sucrose, raffinose, sorbitol, trehalose, Tween 80, mannitol, other sugars and starch, and the like provides a novel oral dosage form of the drug. The dosage form, when administered to a fasted patient, provides at least 80% of the amount of active drug species received by the patient by the dosage form when the patient is fed a high fat meal. The unexpected and sizable reduction in food effect on the uptake of drugs by a fasted or fed patient is useful in the prescription of the drug to a patient undergoing treatment because the patient will receive comparable and therapeutically useful levels of the drug regardless of whether the patient is fed or fasted or on a reduced calorie or reduced fat diet.

In one aspect, particles of a heated homogenate containing a poorly soluble drug can be non-crystalline while the cooled dispersion particles produced as a result of application of a particle stabilizing energetic process can be crystalline. While stirring can induce significant particle growth in a cooled homogenate, stirring does not induce significant particle growth in a cooled dispersion formed from the cooled homogenate by an energetic process. The cooled dispersion thus produced is more robust toward particle Growth than the cooled homogenate. The particles of the cooled dispersion are preferably in the micron and submicron range. Depending on the number of stabilizing processing steps, i.e., volume passes, employed in the preparation of the cooled dispersion, the cooled dispersion can also comprise weakly associated aggregates of particles that can be readily broken up or dispersed or de-aggregated by stirring the dispersion. Preferably, an increase in the number of processing steps from 1 to a range of from 5 to 20. preferably from 10 to 20, can produce fewer and more easily dispersed aggregates. Formulation instability toward stirring can be decreased as a result of the particle stabilizing energizing process.

Microscopically, in the case of fenofibrate as an example of a poorly soluble drug, heated homogenate particles are non-crystalline while cooled dispersion particles produced as a result of application of a particle stabilizing energetic process are solid and crystalline. Importantly, while stirring can induce significant particle growth in a cooled homogenate, stirring does not induce significant particle growth in a cooled dispersion formed from the cooled homogenate. The cooled dispersion thus produced is more robust toward particle size growth than the cooled homogenate. One possible explanation is that the number of nucleation sites for formation of crystals of the poorly soluble drug is substantially increased by application of a particle stabilizing energetic process such as microfluidization in the presence of a surface active substance giving rise to stable small crystalline particles in the micron and submicron range.

In one embodiment of the combination of a statin and microparticles of fenofibrate stabilized by a phospholipid surface active substance of this invention, sometimes hereinafter referred to as Fenostatin and disclosed herein, a desired amount of a statin can be added at any step of the preferred process, but preferably can be added to the cooled homogenate containing fenofibrate just prior to the second stage energetic microfluidization process. This is particularly preferred when the statin is thermally or hydrolytically labile. A desired amount of statin to be present in a dosage form of this invention can be determined in one aspect based on the clinically practiced daily dose amount of the statin. Thus for example, for simvastatin the amount to be added to the cooled homogenate will be between 5% to 30% relative to the amount of fenofibrate, and preferably between 7% to 15%. The statin can be added to the cooled homogenate of fenofibrate as powder or as a solution depending on its solubility in an aqueous carrier used such as 10 mM phosphate buffer at pH 8. In the case of lovastatin, simvastatin, itavastatin and certain others, the lactone ring may open to the corresponding hydroxyacid form or a salt thereof under certain aqueous buffer conditions. In this embodiment, after addition of a desired amount of a statin to the cooled homogenate containing fenofibrate, the cooled homogenate plus the added statin are subjected to the energetic microfluidization process, an example of which is described below.

In the dosage forms of the current invention, the statin can be water soluble, water insoluble, or poorly water soluble.

In the dosage forms of the current invention, particularly when the statin is water insoluble or poorly water soluble, the statin can be in the form of a microparticle or can be a constituent of a microparticle, preferably in the form of a microparticle that is stabilized by one or more surface active substance or is a constituent of a microparticle that is stabilized by one or more surface active substance. In this aspect, a preferred surface active substance comprises a phospholipid.

In the dosage forms of the current invention, the statin is selected from the group consisting of lovastatin, pravastatin, simvastatin, atorvastatin, rosuvastatin, fluvastatin, itavastatin, and cerivastatin. In preferred embodiments of the dosage forms of this invention, the statin can be lovastatin where the lovastatin is present in the range of 2 mg to 50 mg; the statin can be pravastatin present in the range of 2 mg to 50 mg; the statin can be simvastatin where the simvastatin is present in the range of 2 mg to 100 mg; the statin can be atorvastatin where the atorvastatin is present in the range of 2 mg to 100 mg; the statin can be rosuvastatin where the rosuvastatin is present in the range of 2 mg to 100 mg; the statin can be fluvastatin where the fluvastatin is present in the range of 2 mg to 50 mg; the statin is itavastatin where the itavastatin is present in the range of 0.2 mg to 100 mg; the statin is cerivastatin where the cerivastatin is present in the range of 0.05 mg to 2 mg.

A preferred particle stabilizing energetic process is microfluidization for example using a Microfluidix M110EH apparatus. Microfluidization can be accomplished using from 1 to 20 volume passes, preferably from 2 to 20 volume passes, more preferably from 5 to 20 volume passes, and most preferably from 10 to 20 volume passes. Microfluidization can be done in continuous mode or in batch mode. A preferred second temperature range is the second temperature range used for the preparation of the cooled homogenate and is preferably from 1° C. to 40° C., more preferably from 4° C. to 40° C., even more preferably form 4° C. to 20° C. and most preferably from 4° C. to 15° C. A useful pressure range for the preparation of the cooled dispersion is a second pressure range, that is, from 2,000 to about 30,000 psi, preferably from 5,000 to about 20,000 psi, and most preferably from 5,000 to 18,000 psi.

The above described microfluidization process is preferably carried out in absence of air by replacing air with an inert gas such as nitrogen or argon.

Microscopically, in one embodiment of a dosage form of this invention comprising microparticles of fenofibrate and a statin, the cooled dispersion comprises a suspension of crystalline fenofibrate microparticles and statin microparticles. Depending directly on the number of stabilizing processing steps or volume passes employed in the preparation of the cooled dispersion, the cooled dispersion can also comprise weakly associated aggregates of crystalline fenofibrate microparticles and statin microparticles that can be broken up or dispersed or de-aggregated by stirring the suspension or manually shaking the suspension.

FIG. 1 is an optical microscopic comparison of microfluidized fenofibrate with micronized fenofibrate and fenofibrate compositions prepared in the presence of starch. In FIG 1(A), crystals of fenofibrate 20 and domains of starch 10 are large with respect to the 100 micrometer scale. In FIG. 1(B), encircled micronized fenofibrate 40 is seen to be non-uniformly sized and dispersed and particles are entrained in starch domain 30. In FIG. 1(C), encircled microfluidized fenofibrate particles 40 that are stabilized with phospholipid are uniformly distributed in an average size smaller than micronized fenofibrate of FIG. 1(B).

A reduction in the cooled dispersion particle mean diameter can be achieved by increasing the number of volume passes during the cold homogenization step. For example, as shown in Table 3 for a formulation derived from an admixture of 3% Lipoid E80 as the surface active substance and 10% fenofibrate as a poorly water-soluble drug processed first for 10 volume passes to form a heated homogenate containing the drug, cooled according to method 5 to form a transiently stable cooled homogenate containing the drug, and then microfluidized for 2 volume to 10 volume passes to form a cooled dispersion of small particles containing the drug, the observed mean diameter was 0.26 to 0.54 micrometers as a cooled homogenate prior to undergoing a particle stabilizing energizing process, 1.45 micrometers as a cooled dispersion when processed for 2 volume passes, and 0.9 micrometers when processed for 10 volume passes. Surprisingly, formulation stability toward stirring was dramatically increased as a result of the particle stabilizing energizing process. Without the additional particle stabilizing energizing process, the average particle size of the cooled homogenate increased by two orders of magnitude with stirring within 30 minutes. However, after application of the particle stabilizing energizing process, the average particle size did not increase substantially with stirring up to 24 hours. In addition, the average particle size of the cooled dispersion was smaller and remained smaller up to 5 days when the formulation was processed for 10 volume passes.

TABLE 3

Particle size changes of cooled homogenate and cooled dispersion From an admixture of 10% Fenofibrate, 3% Lipoid E80 as the surface active substance in 10 mM phosphate buffer at pH 8, at 4° C.

| | Time (minutes) | Average size not stirred (micrometers) | Average size stirred (micrometers) |
|---|---|---|---|
| Cooled homogenate (10 volume Passes) | 0 | 0.26 | 0.26 |
| | 30 | 0.26 | 14.22 |
| | 60 | 0.54 | 9.44 |

TABLE 3-continued

Particle size changes of cooled homogenate and cooled dispersion From an admixture of 10% Fenofibrate, 3% Lipoid E80 as the surface active substance in 10 mM phosphate buffer at pH 8, at 4° C.

| | Time (minutes) | Average size not stirred (micrometers) | Average size stirred (micrometers) |
|---|---|---|---|
| Cooled dispersion (2 volume Passes) | 0 | 1.45 | 1.45 |
| | 30 | 1.45 | 1.29 |
| | 60 | 1.37 | 1.37 |
| | 1440 | Not measured | 1.12 |
| Cooled dispersion (10 volume passes) | 0 | 0.87 | Not measured |
| | 1140 | 0.93 | Not measured |
| | 5700 | 0.97 | Not measured |

When egg lecithin Lipoid E80 was replaced with phospholipon H100, the cooled homogenate particle size was higher after 10 passes than with Lipoid E80 equivalent (2.3 micrometers versus 0.3 micrometers, respectively). In addition after processing to form a cooled dispersion of small particles containing the drug, a further relative increase in particle size of cooled dispersion was detected. This can be attributed to aggregation of the primary particles. For both the Lipoid E80 formulation and the phospholipon H100 formulation, aggregate sizes could be decreased over time with stirring.

Scanning electron microscopic (SEM) analysis of examples of cooled dispersions prepared originally from fenofibrate and a phospholipid as a surface active substance in the admixture and by 10 volume passes revealed them to exist as single crystalline particles each about 1 micron in mean diameter. Cooled dispersions are approximately comparable to microfluidized formulations of phospholipid and fenofibrate that can be prepared by microfluidization below the melting point of fenofibrate such as according to IDD-P™ technology developed by RTP Pharmna Inc. as described in U.S. Pat. No. 5,091,187 which is hereby incorporated by reference in that microparticles of phospholipid stabilized fenofibrate can be prepared. However, to achieve such particle size reduction without first melting the drug can require substantially more volume passes of microfluidization, for example as many as 200 passes at about 18,000 psi.

In another aspect of this invention, more than one surface active substance can be used to prepare formulations according to this invention. At least one surface active substance is needed to prepare the initial admixture of this invention, and in one aspect can suffice in the preparation of subsequent heated suspensions, heated homogenates, cooled homogenates, cooled dispersions and dried particles (e.g., spray dried and lyophilized) prepared according to this invention. In another aspect, addition of more than one surface active substance can be made to the admixture, the heated suspension, the heated homogenate, the cooled homogenate, and the cooled dispersion of this invention. Such additions can be made at one individual step in the process or at more than one step in the process. For example, a second surface active agent can be added to the admixture or to the heated suspension, and additional amounts of the second surface active agent or a third surface active agent can be added to the cooled homogenate or to the cooled suspension or even to the dried small particles prepared according to this invention.

Preferred compositions of this invention that provide substantial elimination of the food effect observed with fenofibrate alone that has been micronized in the presence of a surfactant such as sodium lauryl sulfate (for example in a jet milling process) and then mixed with a statin or of such fenofibrate that is dosed separately from a statin comprise a combination of phospholipid stabilized microparticles of fenofibrate and a statin in the presence of a sugar such as sucrose, raffinose, sorbitol, trehalose, and the like.

In one embodiment, the total concentration of one or of more than one surface active substance added to the formulations prepared according to this invention can be in the range of 0.1 to 50%, preferably 0.2 to 20%, and more preferably 0.5 to 10%.

In another embodiment, the total concentration of one or of more than one surface active substance added to the formulations prepared according to this invention that comprise phospholipid stabilized microparticles can be in the range of 0.1 to 50%, preferably 0.2 to 20%, and more preferably 0.5 to 10%.

In another aspect of this invention, bulking agents can be added to the admixture, to the heated homogenate, to the cooled homogenate, and to the cooled dispersion. Bulking agents can be added as solids, as mixtures, as solutions in aqueous carrier, and in combinations of solids and solutions. Bulking agents can be added at the beginning or end of the steps leading to the formation of a heated homogenate, cooled homogenate, and cooled dispersion, and they can be added at more than one stage during the process. The amount of total bulking agents that can be added ranges from about 0.1% to about 50%, preferably from 1% to about 30%, and more preferably from about 2% to about 30%. Bulking agents can be added as individual agents at these levels or in combination such that the total amount of bulking agent resides within these levels.

With respect to the compositions and methods of this invention, bulking agents are preferably pharmaceutically acceptable excipients.

Addition of a variety of bulking agents at different steps in the process of this invention does not produce a substantial increase the mean particle diameter of a cooled dispersion over a period of time such as over 24 hours. For example, when bulking agents sorbitol (5%) and sucrose (10%) were added to a 3% Lipoid E80 and 10% fenofibrate admixture and the formulation was processed for 10 passes to form a cooled homogenate and for 10 passes to form a cooled dispersion of small particles containing the drug, the particle size of the cooled dispersion (0.97 micrometers) was very similar in size to that of an analogous formulation composition (i.e., 0.91 micron) where the same bulking agents were added after the formation of the cooled dispersion.

In one embodiment, subsequent to the formation of the cooled dispersion, a statin can be added. The statin can be in the form of a water soluble solid, a water soluble solid that is pre-dissolved in an aqueous medium, or a water insoluble or poorly water soluble solid that is preferably dispersed in an aqueous medium or dispersible in the cooled dispersion or subsequent compositions, more preferably dispersed as microparticles of the statin stabilized by a phospholipid surface active substance that is most preferably compatible with the phospholipid substance used in the stabilization of the microparticles of fenofibrate of this invention.

Dried compositions containing microparticles of fenofibrate stabilized by a phospholipid such as those that can be prepared by drying an aqueous suspension containing microparticles of fenofibrate stabilized by a phospholipid plus a bulking agent such as a sugar (e.g., sucrose, raffinose, trehalose, and individual sugars such as those that can give crystalline sugar states on drying such as by spray drying as well as mixtures of sugars such as sucrose and raffinose and similar mixtures that can give glassy or amorphous or crystalline sugar states on drying such as by lyophilization) can be further blended with a statin and optionally with additional bulking agents and other known pharmaceutically acceptable excipients useful in the preparation of a dosage form or this invention.

Homogenization of the cooled homogenate containing the drug (fenofibrate and optionally a statin added prior to or at this step) can be carried out in equipment suitable for that process. Useful equipment includes but is not limited to commercially available high pressure homogenization equipment such as APV Gaulin M15, Avestin Emulsiflex C5 or C50, MFIC Microfluidizer M110EH. and other microfluidizers and homogenizers. Homogenization can also be carried out using high shear and ultra high shear mechanical mixers and mills and propeller-containing mixers than can impart sufficient turbulence or energy transfer to the particles to form stable small particles of this invention. The apparatus is cooled to maintain the cooled homogenate and cooled dispersion at the second temperature range. Cooling can be done by use of a cooled air bath, a cooled fluid bath such as a water or ice/water bath, or a suitable heat exchanger that is cooled and maintained at or below the second temperature range that is below the melting point of the drug In this aspect of the invention, in an ensuing step of this process to prepare microparticulate fenofibrate or a Fenostatin combination comprising microparticles of fenofibrate and a statin, the cooled dispersion comprising a bulking agent (e.g. sucrose, sorbitol, trehalose, raffinose, or other sugars or combinations thereof) and fenofibrate microparticles optionally in combination with a statin as appropriate can be dried to provide a matrix of small particles containing fenofibrate alone or a combination of fenofibrate and a statin. The microparticles of fenofibrate can comprise a number of possible compositions in this invention. For example, the microparticles of fenofibrate can comprise a substantially solid core of fenofibrate, phospholipid plus fenofibrate in the particle, a mixture of fenofibrate and statin in the same particle, a mixture of fenofibrate and statin in different particles, a mixture of fenofibrate and statin in gradient amounts of fenofibrate and statin in the same distribution of particles, regions of fenofibrate and statin phase separated in the same particle, domains fenofibrate and statin phase separated in the same particle, or other distributions of fenofibrate and statin and phospholipid. Drying can be done using a number of commonly known methods, for example by spray drying, lyophilization, and evaporation. Preferably at least one or more than one bulking agent is present in the formulation undergoing drying.

When drying is done by spray drying, the cooled dispersion of microparticles of fenofibrate stabilized by a surface active substance (preferably a phospholipid) and optionally a statin in suitable form (e.g., in solution, as a dispersion of microparticles, etc.) is fed into the spray dryer as a liquid, preferably at a temperature in the second temperature range and preferably as a dispersion comprising one or more than one bulking agent in an aqueous medium such as a solution of a sugar in an aqueous medium.

In one embodiment of this invention, organic solvents such as water miscible organic solvents can be employed, particularly with the statin or at the drying stage. For example, a water-insoluble or poorly water-soluble statin can be dissolved in a water compatible organic solvent such as methanol, ethanol, isopropanol, acetone, tetrahydrofuran, acetonitrile, or other appropriate solvent including one or more of those previously mentioned herein, optionally together with one or more surface active substance such as a phospholipid or a mixture of phospholipid and a polyoxyethylene-containing surfactant, and the solution can be added to water or other aqueous medium to provide a dispersion of the statin stabilized by the surface active substance(s). The organic solvent can then be removed in the drying process together with the water or distilled from the water prior to drying. Organic solvents such as ethanol and acetone and others can form azeotropic mixtures with water (e.g. binary azeotropes, tertiary azeotropes, etc.). In one aspect, amounts of one or more azeotrope-forming organic solvents can be used sufficient to form an azeotropic mixture with the water of the aqueous medium. The organic solvent (s) and the water can be removed in a drying step such as by spray drying or evaporation. Formation of an azeotrope can have the advantage of lowering the temperature required to evaporate the water from the aqueous mixture. Further, if less than an azeotrope forming quantity of organic solvent is used in this aspect of the invention, the azeotropic composition will be removed at a temperature below that required to remove water, and thus the organic solvent will be more completely removed by an evaporation process.

When drying is done by evaporation, the aqueous carrier of the cooled dispersion can be maintained as a liquid and water (and optionally added organic solvent and/or azeotrope) is removed under reduced pressure and with application of enough heat to keep at least some and preferably all of the aqueous carrier in the cooled dispersion that is drying in the liquid state until it is dried.

In currently preferred embodiments of this invention, an organic solvent is not employed or is not present in the drying step.

When drying is done by lyophilization, the aqueous carrier of the cooled dispersion is frozen and the composition is lyophilized under reduced pressure and application of heat to the frozen suspension to provide a lyophilizate comprising a matrix of small particles containing fenofibrate or a lyophilizate comprising a combination a matrix of small particles containing fenofibrate and a statin. Freezing and lyophilization are preferably done in a conventional freeze dryer, for example, in a Virtis Corporation Unitop freeze dryer using conventional techniques. Freezing can be done using the freezing apparatus in the freeze dryer or by other means such as by freezing using liquefied gas such as liquid nitrogen or by freezing methods employing solid carbon dioxide as a cooling agent.

Lyophilization can be done on frozen dispersions in bulk such as on dispersions added to trays and then frozen or on dispersions that have been added to vials, for example in 2 mL or 10 mL vials, and then frozen. Bulking agents can be added to the formulation to facilitate reconstitution of the lyophilizate.

In compositions of this invention that comprise in an aqueous carrier cooled dispersions containing a combination of fenofibrate and a statin, in a final step of the process the cooled dispersion can be dried by freezing the aqueous carrier in the dispersion and lyophilizing the frozen dispersion under reduced pressure and by application of heat to provide a lyophilizate comprising a matrix of small particles containing fenofibrate and a statin. Optionally, the cooled suspension can be spray dried to provide a dried powder of particles containing fenofibrate and a statin. Alternatively, the water in the aqueous carrier of the cooled dispersion can be evaporated, for example under reduced pressure to provide dried small particles containing fenofibrate and a statin.

By small particles containing a poorly water-soluble drug is meant particles in the range of 0.1 micron to 20 micrometers in average diameter containing a poorly water-soluble drug, preferably in the range of 0.1 to 5 micrometers containing a poorly water-soluble druid, and most preferably in the range of 0.1 to 2 micron containing a poorly water-soluble druo.

By small particles containing fenofibrate is meant particles in the range of 0.1 micron to 20 micrometers in average diameter containing fenofibrate, preferably in the range of 0.1 to 5 micrometers containing fenofibrate, and most preferably in the range of 0.1 to 2 micron containing fenofibrate.

Addition of bulking agents such as sucrose and sorbitol for example to the admixture before processing or to the cooled dispersion just prior to drying provides suspensions of particles which on reconstitution with water or aqueous media are similar in particle size to those of the antecedent cooled dispersion. Drying can be done preferably by lyophilization or spray drying.

Addition of bulking agent such as trehalose either to the admixture before processing, to the heated homogenate, to the cooled homogenate, or to the cooled dispersion just prior to during provides particle size suspensions that on drying and subsequent reconstitution provide dispersions or particles similar in size to those of the antecedent cooled dispersion.

Samples of cooled dispersion can be dried for example by lyophilization with bulking agents and reconstituted in modified simulated gastric fluid (SGF) with gentle inversion immediately after lyophilization. The particle sizes of the dispersions on reconstitution can be similar to, i.e, the same or slightly larger than, those of the antecedent cooled dispersion. Microscopically in one aspect, the reconstituted suspensions can exist primarily as single crystalline particles together with occasional aggregates. For example, a cooled dispersion prepared from an admixture of 3% Lipoid E80 as the surface active substance, 10% fenofibrate, 10% sucrose, and 5% sorbitol as an antecedent cooled dispersion has an average particle size of 0.96 micrometers. On reconstitution of the corresponding lyophilizate, the average particle size of the reconstituted suspension is 1.57 micrometers. For the compositionally equivalent formulation where the bulking agents are added to the cooled dispersion, mean particle diameters before and after lyophilization are 0.91 and 1.38 micrometers, respectively. A statin can be added to these dried fenofibrate compositions by blending as a solid statin or in the form of dried microparticles of statin or dried micronized particles of statin with the dried fenofibrate composition and optionally with additional excipients.

Other bulking agents, for example glycerol at 2%, sucrose at 5%, also yield dried particles that reconstitute easily and provide suspensions of single crystalline particles.

The period of stability of the particles of the cooled dispersion of stabilized small particles containing the drug can extend from the stability period of the transiently stable particles of the cooled homogenate up to several months. Stability of more than a year is also contemplated.

Formulations prepared by this invention may be dried into powders with the addition or blending of binders and other blended excipients known in the art. The resulting blended dried powders invention.

Formulations prepared by this invention may be dried into powders, optionally blended with excipients or bulking agents, and then can be filled into capsules or converted into granules or tablets with the addition of binders and other excipients known in the art of tablet making such as, for example, silica as a flow aid and magnesium stearate.

In one aspect of this invention, the dosage form can be a tablet, preferably a coated tablet such as a film-coated tablet a tablet coated with a moisture resistant or moisture retardant layer such as a hydrophobically substituted polymer that does not readily swell in moist air, a tablet coated with a pharmaceutically acceptable polymer such as a cellulose or chemically modified cellulose derivative, a tablet with a coating containing gelatin, an tablet coated with an enteric coating, a tablet with a coating containing a pharmaceutically acceptable sugar that can be amorphous, a tablet with a coating that can be applied from a liquid, a tablet with a coating that can be sprayed onto the surface of the tablet, a tablet that is encapsulated in a coating, a tablet with a coating that can be applied by a dry coating process, a tablet with a coating that can be applied as a heated or thermally softened or molten substance that is cooled to form a hardened or solid coating, a tablet with a coating that can be applied using electrostatic attraction forces between the tablet and constituents that form the coating, tablet with a other pharmaceutically acceptable coating materials and coating processes.

Another currently preferred dosage form of this invention is a capsule dosage form. A currently preferred formulation composition for oral administration in a capsule dosage form comprises a combination of microparticles of phospholipid stabilized fenofibrate and a statin together with a bulking agent. For example, a preferred composition comprises fenofibrate at 10% w/w in the form of phospholipid stabilized microparticles prepared by microfluidization in 10 mM phosphate buffer with phospholipid Lipoid E80 at 3% w/w, a statin present at 1%, a bulking agent sucrose present at 10% w/w, and an additional bulking agent sorbitol present at 5% w/w. The suspension of microparticles prepared by microfluidization of these ingredients is dried by lyophilization to remove water and form a solid which is blended with colloidal silicon dioxide (up to 1% w/w) and magnesium stearate (up to 5% w/w). This blend is then filled into capsules for oral delivery to a patient.

Alternatively, the above blend can be compressed into tablets that can be optionally coated as described above to form tablets suitable for oral delivery to a patient.

The amount of fenofibrate per capsule or tablet can range from about 20 mg to about 300 mg, and preferably from about 40 mg to about 300 mg, and is most preferably 40 mg, 50 mg, 51 mg, 52 mg, 53 mg, 54 mg, 67 mg, 100 mg, 102 mg, 103 mg, 104 mg, 134 mg, 150 mg, 153 mg, 156 mg, 159 mg, 160 mg, 200 mg, 213 mg, 250 mg, and 300 mg of fenofibrate per capsule or per tablet. Currently most preferred dosage levels contain 50 mg, 67 mg, 100 mg, 134 mg, 150 mg. 160 mg, 200 mg and 213 mg of fenofibrate as microparticles stabilized with phospholipid.

In the compositions of this invention, the statin can be water-soluble or water insoluble or poorly water-soluble. In one aspect of this invention, the dosage forms of this invention can contain water insoluble or poorly water-soluble statins in the form of microparticles such as a phospholipid stabilized microparticles of a solid statin core, or as a constituent of a microparticle such as may occur if the statin is present in a microparticle core comprising fenofibrate. Preferred statins are lovastatin, pravastatin, simvastatin, atorvastatin, rosuvastatin, fluvastatin, itavastatin, and cerivastatin.

The amount of a statin in a dosage form of this invention will depend on which statin is used for the combination formulation. For example, for a combination comprising fenofibrate and simvastatin, the amount of simvastatin per capsule or tablet can range from about 1 mg to about 20 mg and in some cases up to 100 mg, although preferably it will be from 5 mg to about 10 mg.

For a combination comprising fenofibrate and lovastatin, the amount of lovastatin in a dosage form of this invention is in the range of 2 mg to 50 mg although preferably it will be from 10 to 40 mg.

For a combination comprising fenofibrate and pravastatin, the amount of pravastatin in a dosage form of this invention is in the range of 2 mg to 50 mg although preferably it will be from 10 to 40 mg.

For a combination comprising fenofibrate and atorvastatin, the amount of atorvastatin in a dosage form of this invention is in the range of 2 mg to 100 mg although preferably it will be from 5 to 80 mg, and more preferably from 5 to 20 mg.

For a combination comprising fenofibrate and rosuvastatin, the amount of rosuvastatin in a dosage form of this invention is in the range of 2 mg to about 80 mg although preferably it will be from 5 to 20 mg.

For a combination comprising fenofibrate and fluvastatin, the amount of fluvastatin in a dosage form of this invention is in the range of 2 mg to 50 mg although preferably it will be from 20 to 40 mg.

For a combination comprising fenofibrate and itavastatin, the amount of itavastatin in a dosage form of this invention is in the range of 0.1 to about 20 mg although preferably it will be from 2 to 10 mg.

For a combination comprising fenofibrate and cerivastatin, the amount of cerivastatin in a dosage form of this invention is in the range of 0.02 mg to 1.2 mg although preferably it will be from 0.2 to 0.8 mg.

Capsules and tablets for oral administration provide fenofibrate to a human patient in need of treatment that is substantially independent of food effect. Thus, a patient in a fasted state will receive at least 80% of the dose of the drug that the patient in a fed state will receive by taking the same capsule or tablet dosage form. More preferably, a patient in a fasted state will receive at least 85% of the dose of the drug that the patient in a fed state will receive by taking the same capsule or tablet dosage form. Even more preferably, a patient in a fasted state will receive at least 87% of the dose of the drug that the patient in a fed state will receive by taking the same capsule or tablet dosage form. Even more preferably, a patient in a fasted state will receive at least 90% of the dose of the drug that the patient in a fed state will receive by taking the same capsule or tablet dosage form. Yet even more preferably, a patient in a fasted state will receive at least 95% of the dose of the drug that the patient in a fed state will receive by taking the same capsule or tablet dosage form.

Figure 2:
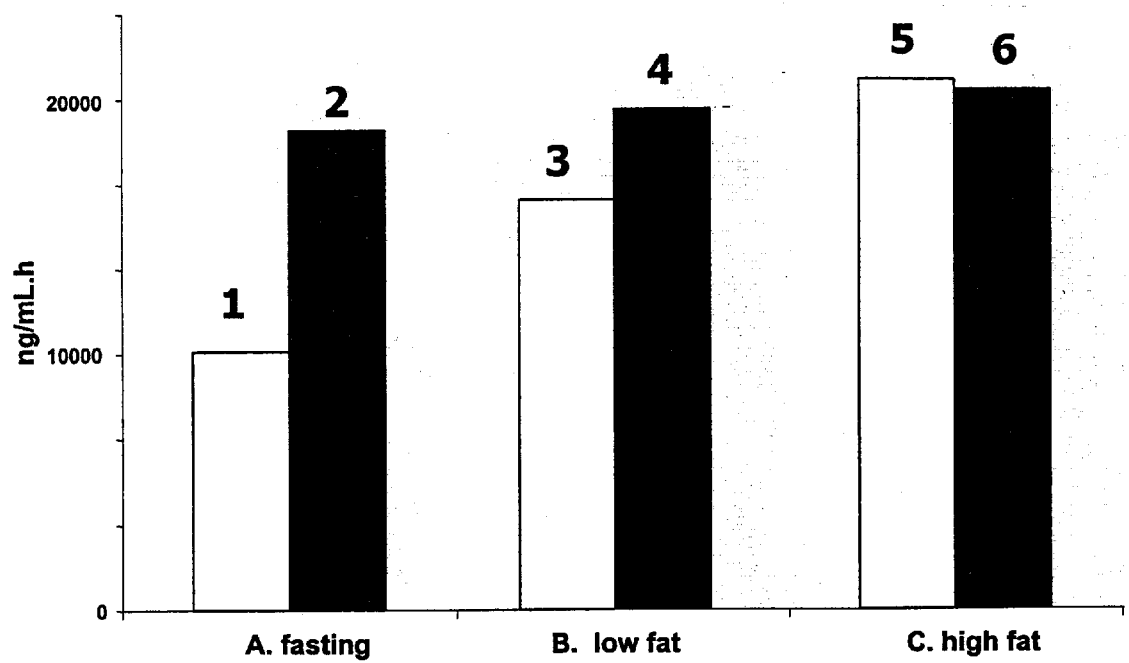
FIG. 2 is a comparison of the oral bioavailability of microparticles of fenofibrate prepared by microfluidization in the presence of a phospholipid stabilizing agent versus the oral bioavailability of micronized fenofibrate under fasting, low fat fed, and high fat fed conditions.

Particles of drug provided according to this invention have bioavailability comparable to or better than similar sized particles prepared by alternate methods. This is illustrated graphically in FIG. 2 which compares the oral bioavailability of microparticles of fenofibrate prepared by microfluidization in the presence of a phospholipid stabilizing agent versus the oral bioavailability of micronized fenofibrate under fasting, low fat fed, and high fat fed conditions. In FIG. 2A, the fenofibrate in microfluidized phospholipid-stabilized microparticles (bar 2) is nearly twice as bioavailable as that in a micronized formulation (bar 1) in the fasted state. In FIG. 2B, the fenofibrate in microfluidized phospholipid-stabilized microparticles (bar 4) is more bioavailable than that in a micronized formulation (bar 3) in a low fat fed state. In FIG. 2C, there is no significant difference in bioavailability between the fenofibrate in microfluidized phospholipid-stabilized microparticles (bar 6) and in a micronized formulation (bar 5). Bioavailability of fenofibrate increases by more than a factor of two when comparing bars 1, 3, and 5 that refer to a micronized formulation of fenofibrate. However, bioavailability of fenofibrate is approximately constant when comparing bars 2, 4, and 6 that refer to fenofibrate in a microfluidized phospholipid-stabilized microparticle formulation. The bioavailability of fenofibrate in formulations of microfluidized phospholipid-stabilized microparticles is seen to increase by less than 25% when comparing fasting and high fat fed conditions (bars 2 and 6), preferably increasing by less than 20%, and more preferably by less than 15% (bars 2 and 6). The clinical data used to produce bars 2 and 6 indicate an increase of 14% in the bioavailability of fenofibrate between fasted and high fat fed conditions, i.e., a factor of 1.14 between bioavailabilities represented by bar 2 (fasted) versus bar 6 (high fat fed). Blood levels of fenofibric acid, the fenofibrate active species, were measured to obtain the data from which FIG. 2 was generated.

This invention provides a dosage form of a pharmaceutical composition comprising a combination of a statin and microparticles of fenofibrate that are stabilized by a phospholipid surface active substance, wherein the dosage form provides to a patient in need of treatment by the statin and fenofibrate a therapeutically effective dose of the statin and a therapeutically effective quantity of fenofibrate active species to said patient when fasted that is at least 80% of the quantity of fenofibrate active species provided by said amount to said patient when fed a meal containing fat.

This invention also provides a dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is greater than 80% of the quantity of fenofibrate active species provided by said amount to said patient when fed at least 1000 calories 50% of which are from fat.

The invention also provides an oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species into the blood of said patient when fasted that is between 85% and 115% of the quantity of fenofibrate active species provided by said amount into the blood of said patient when fed at least 1000 calories 50% of which are from fat.

This invention also provides an oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is at least 85% of the AUC quantity of fenofibrate active species provided by said amount to said patient when fed at least 1000 calories 50% of which are from fat.

The amount of a given statin in a dosage form of this invention can be the same as the amount of that statin in currently available dosage forms of that statin alone such as those listed previously, or it can be an amount that is lower than the amount of that statin in currently available dosage forms of that statin alone. The presence of the statin augments or supplements the effect of the fenofibrate of this invention, and the presence of the fenofibrate augments or supplements the effect of the statin. Thus, a therapeutically effective dosage form of this invention containing a statin and fenofibrate can have relatively lower amounts of the statin, relatively lower amounts of fenofibrate, or relatively lower amounts of both than the amount of the statin when in a dosage form without fenofibrate or than the amount of fenofibrate when in a dosage form without the statin, or both.

The dosage forms of this invention can be prepared by a process comprising blending dried small particles containing fenofibrate stabilized by a phospholipid surface active substance with a statin and optionally with one or more pharmaceutically acceptable excipients such a one or more sugars (e.g., sucrose, raffinose, sorbitol, and trehalose).

The dosage forms of this invention can be prepared by a process comprising blending dried small particles containing fenofibrate stabilized by a phospholipid surface active substance with a statin and with a bulking agent comprising a sugar and optionally with one or more pharmaceutically acceptable excipients such a one or more additional sugars (e.g., sucrose, raffinose, sorbitol, and trehalose).

Dosage forms of this invention can be administered to a patient in need of treatment by a combination of a statin and fenofibrate can be administered several times a day such as three or four times a day, but more preferably twice a day, and most preferably once a day. Preferably, the more frequent the administration of the drug, the smaller the quantity of the drug contained in a given dosage form.

This invention further comprises a method of treatment of dyslipidemia. This invention further comprises a method of treatment of dyslipidemia where the dyslipidemia comprises hypercholesterolemia, hyperlipidemia, hypertrigylceridaemia or combinations thereof.

This invention further comprises a method of treatment of dyslipidemia and dyslipoproteinemia in a patient comprising the administration to said patient of a dosage form of a pharmaceutical composition comprising a combination of a statin and microparticles of fenocibrate that are stabilized by a phospholipid surface active substance, wherein the dosage form provides to a patient in need of treatment by the statin and fenofibrate a therapeutically effective dose of the statin and a therapeutically effective quantity of fenofibrate active species to said patient when fasted that is at least 80% of the quantity of fenofibrate active species provided by said amount to said patient when fed a meal containing fat.

This invention further comprises a method of treatment of dyslipidemia and dyslipoproteinemia in a patient comprising the administration to said patient of a dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is greater than 80% of the quantity of fenofibrate active species provided by said amount to said patient when fed at least 1000 calories 50% of which are from fat.

This invention further comprises a method of treatment of dyslipidemia and dyslipoproteinemia in a patient comprising the administration to said patient of an oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species into the blood of said patient when fasted that is between 85% and 115% of the quantity of fenofibrate active species provided by said amount into the blood of said patient when fed at least 1000 calories 50% of which are from fat.

This invention further comprises a method of treatment of dyslipidemia and dyslipoproteinemia in a patient comprising the administration to said patient of an oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is at least 85% of the AUC quantity of fenofibrate active species provided by said amount to said patient when fed at least 1000 calories 50% of which are from fat.

While a preferred method of preparation of microparticles of fenofibrate stabilized with phospholipid comprises a microfluidization process, other methods of preparation of micropaiticles of fenofibrate can find utility in this invention. For example, it is possible to prepare microparticles of fenofibrate stabilized with phospholipid using a sonication process; using a milling process such as media milling, jet milling, ball milling, attrition milling and the like; using a precipitation process such as precipitation of drug from a solvent miscible with water in the presence of a phospholipid to form a suspension of microparticles; using an emulsification process; using a solvent evaporation process such as a solvent spray process; using a particle preparation process that utilizes a liquefied gas; and using a particle preparation process that utilizes a supercritical fluid. Microparticles of fenofibrate prepared according to these known methods and stabilized with a phospholipid can be formulated with a statin in the presence of the bulking agents and prepared into dosage forms for use in patients as described herein.

The invention is additionally illustrated in connection with the following examples, which are considered to be illustrative of the present invention. It should be understood, however, that the invention is not limited to the specific details of the Examples.

EXAMPLE 1

A mixture of 60 parts of Lipoid E80 as the surface active substance and 200 parts of a poorly water-soluble drug, fenofibrate, is homogeneously dispersed in 1440 parts of 10 mM pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous-high shear mixing at 2,500 to 4,000 rpm. The heated suspension is then recirculatively homogenized for 10 batch volume cycles or passes using a Microfluidizer M110Y operated at 3,400 to 3,600 psig while maintained at 85° C. to 99° C. to form a heated homogenate containing the drug. After 10 passes, the heated homogenate is cooled by passage through a heat exchanger cooled by chilled water at 5° C. to 10° C. to provide a transiently stable cooled homogenate. To the cooled homogenate is added 10–30 parts of simvastatin and the cooled homogenate plus statin is further homogenized for 10 to 20 batch volume cycles or passes using a Microfluidics M110 EH homogenizer operated at 18,000 psig (peak) while maintained at 4° C. to 13° C. The resulting cooled dispersion comprising the statin and small particles containing fenofibrate of size less than 1.0 micron in diameter is then dried by freezing to about −40° C. and lyophilized under vacuum to produce a matrix of dried small particles containing fenofibrate and the simvastatin.

EXAMPLE 2

A mixture of 60 parts of Lipoid E80 as the surface active substance and 200 parts of a poorly water-soluble drug, fenofibrate, is homogeneously dispersed in 1440 parts of 10 mM pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained at 85° C. to 99° C. to form a heated homogenate containing the drug. After 10 passes, the heated homogenate is cooled by passage through a heat exchanger cooled by chilled water at 5° C. to 10° C. and the transiently stable cooled homogenate is further homogenized for 10 to 20 batch volume cycles or passes using a Microfluidics M110 EH homogenizer operated at 18,000 psig (peak) while maintained at 4° C. to 13° C. Alternatively appropriate amounts of bulking agents are added to the cooled homogenate before the microfluidization with M110 EH. The resulting cooled dispersion comprising small particles containing fenofibrate of size less than 1.0 micron in diameter is then dried by freezing to about −40° C. and lyophilized under vacuum to produce a matrix of dried small particles containing fenofibrate.

EXAMPLE 3

A mixture of 60 parts of Lipoid E80 as the surface active substance and 200 parts of a poorly water-soluble drug, fenofibrate, is homogeneously dispersed in 1440 parts of 10 mM pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained at 85° C. to 99° C. to form a heated homogenate containing the drug. After 10 passes, the heated homogenate is cooled by passage through a heat exchanger cooled by chilled water at 5° C. to 10° C. and the transiently stable cooled homogenate is further homogenized for 10 to 20 batch volume cycles or passes using a Microfluidics M110 EH homogenizer operated at 18,000 psig (peak) while maintained at 4° C. to 13° C. Between 1–2 parts of cerivastatin dissolved in 10 parts of 10 mM aqueous phosphate buffer, pH 8.0 is added to the resulting cooled dispersion. The suspension is further mixed with a ProScientific 400 high shear mixer at 2000 to 3000 rpm at 5° C. to 15° C. for 15 minutes. The resulting suspension comprising small particles of fenofibrate of size less than 1.0 micron in diameter and dissolved cerivastatin is then dried by freezing to about −40° C. and lyophilization under vacuum to produce a matrix of dried small particles containing fenofibrate and cerivastatin.

EXAMPLE 4

A mixture of 60 parts of Lipoid E80 as the surface active substance and 200 parts of a poorly water-soluble drug, fenofibrate, is homogeneously dispersed in 1440 parts of 10 mM pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to form a heated homogenate containing drug. After 10 passes, the heated homogenate is cooled by passage through a heat exchanger chilled with ice water, and to the transiently stable cooled homogenate is added 10 to 30 parts of simvastatin followed by further homogenization for 10 to 20 batch volume cycles or passes using a Microfluidics M110 EH homogenizer operated at 18,000 psig (peak) while maintained between 4° C. and 15° C. The resulting cooled dispersion comprising small particles containing the drug of size less than 1.0 micron in diameter is treated with a solution of 200 parts of sucrose plus 100 parts of sorbitol as bulking agents in additional aqueous carrier and is then dried by freezing in liquid nitrogen and lyophilization under vacuum to produce a matrix of dried small particles containing fenofibrate and simvastatin.

EXAMPLE 5

A mixture of 60 parts of Lipoid E80 as the surface active substance and 200 parts of a poorly water-soluble drug, fenofibrate, is homogeneously dispersed in 1440 parts of 10 meal pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to form a heated homogenate containing drug. After 10 passes, the heated homogenate is cooled by passage through a heat exchanger chilled with ice water, kept at 4° C. for 30 min, and the transiently stable cooled homogenate is further homogenized for 10 to 20 batch volume cycles or passes using a Microfluidics M110 EH homogenizer operated at 18,000 psig (peak) while maintained between 4° C. and 15° C. Between 1 to 2 parts of cerivastatin dissolved in 10 parts of 10 mM aqueous phosphate buffer, pH 8.0 is added to the resulting cooled dispersion. The suspension is further mixed with a ProScientific 44 high shear mixer at 2000 to 3000 rpm at 5° C. to 15° C. for 15 minutes. The resulting suspension comprising small particles of fenofibrate of size less than 1.0 micron in diameter and dissolved cerivastatin is treated with a solution of 200 parts of sucrose plus 100 parts of sorbitol as bulking agents in additional aqueous carrier and is then dried by freezing in liquid nitrogen and lyophilization under vacuum to produce a matrix of dried small particles containing fenofibrate and cerivastatin.

What is claimed is:

1. A dosage form of a pharmaceutical composition comprising a combination of a statin and microparticles of fenofibrate that are stabilized by a phospholipid surface active substance, wherein the dosage form provides to a patient in need of treatment by the statin and fenofibrate a therapeutically effective dose of the statin and a therapeutically effective quantity of fenofibrate active species to said patient when fasted that is at least 80% of the quantity of fenofibrate active species provided by said amount to said patient when fed a meal containing fat.

2. A dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is greater than 80% of the quantity of fenofibrate active species provided by said amount to said patient when fed at least 1000 calories 50% of which are from fat.

3. An oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species into the blood of said patient when fasted that is between 85% and 115% of the quantity of fenofibrate active species provided by said amount into the blood of said patient when fed at least 1000 calories 50% of which are from fat.

4. An oral dosage form of a pharmaceutical composition comprising a combination of a statin and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is at least 85% of the AUC quantity of fenofibrate active species provided by said amount to said patient when fed at least 1000 calories 50% of which are from fat.

5. The dosage form of claim 1 wherein the microparticles of fenofibrate have been prepared in the presence of the phospholipid surface active substance.

6. The dosage form of claim 1 where the statin is water-soluble.

7. The dosage form of claim 1 where the statin is water insoluble or poorly water-soluble.

8. The dosage form of claim 7 where the statin is in the form of a microparticle or is a constituent of a microparticle.

9. The dosage form of any of claim 1 where the statin is in the form of a microparticle that is stabilized by one or more surface active substance or is a constituent of a microparticle that is stabilized by one or more surface active substance.

10. The dosage form of claim 9 where the surface active substance comprises a phospholipid.

11. The dosage form of any of claim 1 where the statin is selected from the group consisting of lovastatin, pravastatin, simvastatin, atorvastatin, rosuvastatin, fluvastatin, itavastatin, and cerivastatin.

12. The dosage form of claim 1 where the statin is lovastatin.

13. The dosage form of claim 12 where the lovastatin is present in the range of 2 mg to 50 mg.

14. The dosage form of claim 1 where the statin is pravastatin.

15. The dosage form of claim 14 where the pravastatin is present in the range of 2 mg to 50 mg.

16. The dosage form of claim 1 where the statin is simvastatin.

17. The dosage form of claim 16 where the simvastatin is present in the range of 2 mg to 100 mg.

18. The dosage form of claim 1 where the statin is atorvastatin.

19. The dosage form of claim 18 where the atorvastatin is present in the range of 2 mg to 100 mg.

20. The dosage form of claim 1 where the statin is rosuvastatin.

21. The dosage form of claim 20 where the rosuvastatin is present in the range of 2 mg to 100 mg.

22. The dosage form of claim 1 where the statin is fluvastatin.

23. The dosage form of claim 22 where the fluvastatin is present in the range of 2 mg to 50 mg.

24. The dosage form of claim 1 where the statin is itavastatin.

25. The dosage form of claim 24 where the itavastatin is present in the range of 0.2 mg to 100 mg.

26. The dosage form of claim 1 where the statin is cerivastatin.

27. The dosage form of claim 26 where the cerivastatin is present in the range of 0.05 mg to 2 mg.

28. The dosage form of claim 1 where the fenofibrate is a solid.

29. The dosage form of claim 1 where the fenofibrate is crystalline.

30. The dosage form of claim 1 where the microparticles have a volume weighted mean size smaller than 5 micrometers.

31. The dosage form of claim 1 where the microparticles have a volume weighted mean size smaller than 4 micrometers.

32. The dosage form of claim 1 where the microparticles have a volume weighted mean size smaller than 3 micrometers.

33. The dosage form of claim 1 where the microparticles have a volume weighted mean size smaller than 2 micrometers.

34. The dosage form of claim 1 where the microparticles have a volume weighted mean size smaller than 1 micrometers.

35. The dosage form of claim 1 where the microparticles have a volume weighted mean size smaller than 0.5 micrometers.

36. The dosage form of claim 1 where the microparticles have been prepared by a process selected from the group consisting of homogenization, microfluidization, hot melt microfluidization, and sonication.

37. The dosage form of claim 1 where the microparticles have been prepared by a process selected from the group consisting of a milling process, a precipitation process, an emulsification process, a solvent evaporation spray process, a particle preparation process that utilizes a liquefied gas, and a particle preparation process that utilizes a supercritical fluid.

38. The dosage form of claim 1 that contains a weight of fenofibrate in the range from 40 mg to 300 mg.

39. The dosage form of claim 1 that contains a weight of fenofibrate selected from the group consisting of 40 mg, 50 mg, 51 mg, 52 mg, 53 mg, 54 mg, 67 mg, 100 mg, 102 mg, 103 mg, 104 mg, 134 mg, 150 mg, 153 mg, 156 mg, 159 mg, 160 mg, 200 mg, 213 mg, 250 mg, and 300 mg of fenofibrate.

40. The dosage form of claim 1 further comprising one or more pharmaceutically acceptable excipient.

41. The dosage form of claim 1 further comprising one or more excipients selected from the group consisting of monosaccharides, disaccharides, trisaccharides, sucrose, raffinose, lactose, mannitol, sorbitol, trehalose, glycerol, dextrose, fructose, pentoses, hexoses, xylitol, and mixtures thereof.

42. The dosage form of claim 1 wherein the phospholipid surface active substance comprises a mixture of phospholipids.

43. The dosage form of claim 1 wherein the phospholipid surface active substance is selected from the group consisting of saturated phospholipids, unsaturated phospholipids, naturally derived phospholipids, synthetic phospholipids, and semisynthetic phospholipids.

44. The dosage form of claim 1 wherein the phospholipid surface active substance is selected from the group consisting of Lipoid E80, Lipoid EPC, Lipoid SPC, DMPG, Phospholipon 100H, a hydrogenated soybean phosphatidylcholine, Phospholipon 90H, Lipoid SPC-3, egg phospholipid, purified egg phopholipid, and mixtures thereof.

45. The dosage form of claim 1 that comprises a capsule.

46. The dosage form of claim 1 that comprises a tablet.

47. The dosage form of claim 1 that comprises a powder dispersible in water or a beverage.

48. The dosage form of claim 1 further comprising a bulking agent.

49. The tablet of claim 46 selected from the group consisting of a film-coated tablet, a moisture resistant tablet, and a tablet coated with a pharmaceutically acceptable polymer.

50. A capsule or tablet dosage form for oral administration comprising a pharmaceutically effective amount of a composition containing a statin and small particles of a fibrate stabilized by a phospholipid stabilizing agent, a sugar, and optionally a carbohydrate-derived alcohol wherein said amount of said dosage form provides a therapeutically effective dose of the statin and a therapeutically effective level of fibrate active species into the blood of a patient in a fasted state that differs by less than 20% of the level of said fibrate active species that said patient receives in a fed state.

51. A dosage form of a pharmaceutical composition comprising a combination of a statin, a carbohydrate bulking agent, and microparticles of fenofibrate that are stabilized by a phospholipid surface active substance, wherein the dosage form provides to a patient in need of treatment by the statin and fenofibrate a therapeutically effective dose of the statin and a therapeutically effective quantity of fenofibrate active species to said patient when fasted that is at least 80% of the quantity of fenofibrate active species provided by said amount to said patient when fed a meal containing fat.

52. A dosage form of a pharmaceutical composition comprising a combination of a statin, a carbohydrate bulking agent, and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is greater than 80% of the quantity of fenofibrate active species provided by said amount to said patient when fed at at least 1000 calories 50% of which are from fat.

53. An oral dosage form of a pharmaceutical composition comprising a combination of a statin, a carbohydrate bulking agent, and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species into the blood of said patient when fasted that is between 85% and 115% of the quantity of fenofibrate active species provided by said amount into the blood of said patient when fed at least 1000 calories 50% of which are from fat.

54. An oral dosage form of a pharmaceutical composition comprising a combination of a statin, a carbohydrate bulking agent, and microparticles of fenofibrate that are stabilized by a phospholipid surface active substance, wherein the dosage form provides to a human patient in need of treatment by the statin and fenofibrate a therapeutically effective dose of the statin and a therapeutically effective quantity of fenofibrate active species to said patient when fasted that is at least 85% of the AUC quantity of fenofibrate active species provided by said amount to said patient when fed at least 1000 calories 50% of which are from fat.

55. The dosage form of claim 51 wherein the microparticles of fenofibrate have been prepared in the presence of the phospholipid surface active substance.

56. The dosage form of claim 51 where the statin is water-soluble.

57. The dosage form of claim 51 where the statin is water insoluble or poorly water-soluble.

58. The dosage form of claim 57 where the statin is in the form of a microparticle or is a constituent of a microparticle.

59. The dosage form of claim 51 where the statin is in the form of a microparticle that is stabilized by one or more surface active substance or is a constituent of a microparticle that is stabilized by one or more surface active substance.

60. The dosage form of claim 59 where the surface active substance comprises a phospholipid.

61. The dosage form of claim 51 where the statin is selected from the group consisting of lovastatin, pravastatin, simvastatin, atorvastatin, rosuvastatin, fluvastatin, itavastatin, and cerivastatin.

62. The dosage form of claim 51 where the statin is lovastatin.

63. The dosage form of claim 62 where the lovastatin is present in the range of 2 mg to 50 mg.

64. The dosage form of claim 51 where the statin is pravastatin.

65. The dosage form of claim 64 where the pravastatin is present in the range of 2 mg to 50 mg.

66. The dosage form of claim 51 where the statin is simvastatin.

67. The dosage form of claim 66 where the simvastatin is present in the range of 2 mg to 100 mg.

68. The dosage form of claim 51 where the statin is atorvastatin.

69. The dosage form of claim 68 where the atorvastatin is present in the range of 2 mg to 100 mg.

70. The dosage form of claim 51 where the statin is rosuvastatin.

71. The dosage form of claim 70 where the rosuvastatin is present in the range of 2 mg to 100 mg.

72. The dosage form of claim 51 where the statin is fluvastatin.

73. The dosage form of claim 72 where the fluvastatin is present in the range of 2 mg to 50 mg.

74. The dosage form of claim 51 where the statin is itavastatin.

75. The dosage form of claim 74 where the itavastatin is present in the range of 0.2 mg to 100 mg.

76. The dosage form of claim 51 where the statin is cerivastatin.

77. The dosage form of claim 76 where the cerivastatin is present in the range of 0.05 mg to 2 mg.

78. The dosage form of claim 51 where the fenofibrate is a solid.

79. The dosage form of claim 51 where the fenofibrate is crystalline.

80. The dosage form of claim 51 where the microparticles have a volume weighted mean size smaller than 5 micrometers.

81. The dosage form of claim 51 where the microparticles have a volume weighted mean size smaller than 4 micrometers.

82. The dosage form of claim 51 where the microparticles have a volume weighted mean size smaller than 3 micrometers.

83. The dosage form of claim 51 where the microparticles have a volume weighted mean size smaller than 2 micrometers.

84. The dosage form of claim 51 where the microparticles have a volume weighted mean size smaller than 1 micrometers.

85. The dosage form of claim 51 where the microparticles have a volume weighted mean size smaller than 0.5 micrometers.

86. The dosage form of claim 51 where the microparticles have been prepared by a process selected from the group consisting of homogenization, microfluidization, hot melt microfluidization, and sonication.

87. The dosage form of claim 51 where the microparticles have been prepared by a process selected from the group consisting of a milling process, a precipitation process, an emulsification process, a solvent evaporation spray process, a particle preparation process that utilizes a liquefied gas, and a particle preparation process that utilizes a supercritical fluid.

88. The dosage form of claim 51 that contains a weight of fenofibrate in the range from 40 mg to 300 mg.

89. The dosage form of claim 51 that contains a weight of fenofibrate selected from the group consisting of 40 mg, 50 mg, 51 mg, 52 mg, 53 mg, 54 mg, 67 mg, 100 mg, 102 mg, 103 mg, 104 mg, 134 mg, 150 mg, 153 mg, 156 mg, 159 mg, 160 mg, 200 mg, 213 mg, 250 mg, and 300 mg of fenofibrate.

90. The dosage form of claim 51 further comprising one or more pharmaceutically acceptable excipient.

91. The dosage form of claim 51 where the carbohydrate is a sugar.

92. The dosage form of claim 51 where the carbohydrate is selected from the group consisting of monosaccharides, disaccharides, trisaccharides, sucrose, raffinose, lactose, mannitol, sorbitol, trehalose, glycerol, dextrose, fructose, pentoses, hexoses, xylitol, and mixtures thereof.

93. The dosage form of claim 51 wherein the phospholipid surface active substance comprises a mixture of phospholipids.

94. The dosage form of claim 51 wherein the phospholipid surface active substance is selected from the group consisting of saturated phospholipids, unsaturated phospholipids, naturally derived phospholipids, synthetic phospholipids, and semisynthetic phospholipids.

95. The dosage form of claim 51 wherein the phospholipid surface active substance is selected from the group consisting of Lipoid E80, Lipoid EPC, Lipoid SPC, DMPG, Phospholipon 100H, a hydrogenated soybean phosphatidylcholine, Phospholipon 90H, Lipoid SPC-3, egg phospholipid, purified egg phopholipid, and mixtures thereof.

96. The dosage form of claim 51 that comprises a capsule.

97. The dosage form of claim 51 that comprises a tablet.

98. The dosage form of claim 51 that comprises a powder dispersible in water or a beverage.

99. The dosage form of claim 51 prepared by a process comprising blending dried small particles containing fenofibrate stabilized by a phospholipid surface active substance with a statin.

100. The dosage form of claim 51 further comprising one or more pharmaceutically acceptable excipients.

101. The tablet of claim 97 selected from the group consisting of a film-coated tablet, a moisture resistant tablet, and a tablet coated with a pharmaceutically acceptable polymer.

* * * * *